US007361463B2

(12) United States Patent
Kaelin, Jr. et al.

(10) Patent No.: US 7,361,463 B2
(45) Date of Patent: Apr. 22, 2008

(54) MUTEINS OF HYPOXIA INDUCIBLE FACTOR ALPHA AND METHODS OF USE THEREOF

(75) Inventors: William G. Kaelin, Jr., Boston, MA (US); Mircea Ivan, Cambridge, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 10/854,483

(22) Filed: May 26, 2004

(65) Prior Publication Data

US 2004/0219635 A1 Nov. 4, 2004

Related U.S. Application Data

(63) Continuation of application No. 10/101,816, filed on Mar. 19, 2002, now Pat. No. 6,849,718.

(60) Provisional application No. 60/345,132, filed on Dec. 20, 2001, provisional application No. 60/342,598, filed on Dec. 20, 2001, provisional application No. 60/345,131, filed on Dec. 20, 2001, provisional application No. 60/345,200, filed on Nov. 9, 2001, provisional application No. 60/332,334, filed on Nov. 9, 2001, provisional application No. 60/332,493, filed on Nov. 9, 2001, provisional application No. 60/277,440, filed on Mar. 20, 2001, provisional application No. 60/277,431, filed on Mar. 20, 2001, provisional application No. 60/277,425, filed on Mar. 20, 2001.

(51) Int. Cl.
*C12Q 1/18* (2006.01)
*C12P 21/06* (2006.01)
*C12N 1/20* (2006.01)
*C12N 15/74* (2006.01)
*C07H 21/04* (2006.01)

(52) U.S. Cl. .................. 435/6; 435/69.1; 435/325; 435/252.3; 435/320.1; 536/23.5

(58) Field of Classification Search ............... 536/23.5; 435/69.1, 325, 252.3, 320.1, 6
See application file for complete search history.

(56) References Cited

U.S. PATENT DOCUMENTS

| 5,882,914 | A | 3/1999 | Semenza |
| 6,124,131 | A | 9/2000 | Semenza |
| 6,222,018 | B1 | 4/2001 | Semenza |
| 6,403,764 | B1* | 6/2002 | Dubaquie et al. |
| 2002/0048794 | A1* | 4/2002 | Poellinger et al. |

FOREIGN PATENT DOCUMENTS

| WO | WO 0010578 | 3/2000 |
| WO | WO 02/12326 A2 * | 2/2002 |

OTHER PUBLICATIONS

Attwood TK. Genomics. The Babel of bioinformatics. Science. 290(5491):471-473, 2000.*
Burgess, et al. Possible dissociation of the heparin-binding and mitogenic activities of heparin-binding growth factor-1 from its receptor-binding activities by site-directed mutagenesis of a single lysine residue. J Cell Biol. 111:2129-2138, 1990.*
Metzler et al. Solution structure of human CTLA-4 and delineation of a CD80/CD86 binding site conserved in CD28, Nat Struc Biol. 4(7):527-531, 1997.*
Skolnick et al. From genes to protein structure and function: novel applications of computational approaches in the genomic era. Trends Biotechnol. 18(1):34-9, 2000.*
Lazar E et al., Transforming growth factor alpha: mutation of aspartic acid 47 and leucine 48 results in different biological activities. Mol Cell Biol. 8:1247-1252, 1988.*
Mountain A. Gene therapy: the first decade. Trends Biotechnol. Mar. 2000;18(3):119-28.*
Ivan et al. HIFalpha targeted for VHL-mediated destruction by proline hydroxylation: implications for O2 sensing. Science. 2001 Apr. 20; 292(5516): 464-8. Epub 2001 Apr. 5.*
GenBank Accession No. BAB70608 (Oct. 23, 2001).
GenBank Accession No. BAB69689 (Jan. 18, 2002).
GenBank Accession No. BAA34234 (Oct. 11, 2001).
M. Ivan, W. G. Kaelin, *Curr. Opin. Gen. and Dev.* Nov. 27, 2001.
Jelkmann *Physiol. Rev.* 72:449-489, 1992.
White et al., *Circ. Res.* 71:1490-1500, 1992.
Wolfe et al., *Eur. J. Biochem.* 135:405-412, 1983.
Semenza, *Hematol. Oncol. Clinics N. Amer.* 8:863-884, 1994.
Goldberg & Schneider, *J. Biol. Chem.* 269:4355-4359, 1994.
Semenza et al., *J. Biol. Chem.* 269:23757-23763, 1994.
Wang & Semenza, *Proc. Natl. Acad. Sci. USA* 90:4304-4308, 1993.
Wang, G.L., and Semenza, G.L., *Blood.* 82:3610-5 (1993).
Jiang, B.H., et al., *J. Biol. Chem.* 272:19253-19260, 1997.
Semenza, G.L., et al., *Kid. Int.* 51:553-555, 1997.
Jiang, B.H., et al., *Am J. Physiol.* 271:C1172-C1180, 1996.
Jiang, B.-H., et al., *J. Biol. Chem.* 271:17771-17778, 1996.
G. Semenza, *Annu. Rev. Cell Dev. Biol.* 15, 551-578 (1999).
R. Wenger, *J Exper Biol* 203, 1253-1263 (2000).
G. Semenza, *Cell* 98, 281-4 (1999).
H. Zhu, F. Bunn, *Resp. Phys.* 115, 239-247 (1999).
C. E. Stebbins, W. G. Kaelin, N. P. Pavletich, *Science* 284, 455-461 (1999).
M. Ohh, et al., *Nature Cell Biology* 2, 423-427 (2000).

(Continued)

*Primary Examiner*—Maher M. Haddad
(74) *Attorney, Agent, or Firm*—Ivor R. Elrifi; Cynthia Kozakiewicz; Mintz, Levin, Cohn, Ferris, Glovsky and Popeo, PC

(57) ABSTRACT

The present invention provides hypoxia inducible factor alpha muteins, DNA sequences encoding these hypoxia inducible factor alpha muteins, recombinant DNA molecules containing those DNA sequences operatively linked to expression control sequences and capable of inducing expression of an hypoxia inducible factor alpha muteins, hosts transformed with those recombinant DNA molecules, pharmaceutical compositions containing hypoxia inducible factor alpha muteins and methods of using those compositions to treat hypoxia and ischemic related tissue damage.

6 Claims, 14 Drawing Sheets

OTHER PUBLICATIONS

T. Kamura, et al., *Proc. Natl. Acad. Sci.* (USA) 97, 10430-10435 (2000).
M. Cockman, et al., *J Biol Chem* 275, 25733-41 (2000).
K. Tanimoto, Y. Makino, T. Pereira, L. Poellinger, *EMBO J* 19, 4298-4309 (2000).
P. Maxwell, et al., *Nature* 399, 271-5 (1999).
R. Deshaies, *Annu Rev Cell Dev Biol* 15, 435-67 (1999).
D. Chowdary, J. Dermody, K. Jha, H. Ozer, *Mol Cell Biol* 14, 1997-2003 (1994).
V. Srinivas, L. Zhang, X. Zhu, J. Caro, *Biochem Biophys Res Commun* 260, 557-61 (1999).
C. Pugh, J. O'Rourke, M. Nagao, J. Gleadle, P. Ratcliffe, *J Biol Chem* 272, 11205-14 (1997).
K. I. Kivirikko, J. Myllyharju, Matrix *Biology* 16, 359-368 (1998).
O. Iliopoulos, A. Kibel, S. Gray, W. G. Kaelin, *Nature Medicine* 1, 822-826 (1995).
Y. Takahashi, S. Takahashi, Y. Shiga, T. Yoshimi, T. Miura, *J Biol Chem* 275, 14139-46 (2000).
M. Bickel, et al., *Hepatology* 28, 404-11 (1998).
T. Franklin, W. Morris, P. Edwards, M. Large, R. Stephenson, *Biochem J* 353, 333-338 (2001).
L. Friedman, et al., *Proc Natl Acad Sci* U S A 97, 4736-41 (2000).
International Search Report for PCT/US02/08946, mailed Sep. 23, 2002.
Masson, et al. Eur. Mol. Bio. Org., 201, 5195-5206, Sept. 2001.

* cited by examiner

FIG. 2E

```
                            *
hHIF-1α   556  DLDLEMLAPYIPMD-DDFQLR   575
hHIF-2α        ELDLETLAPYIPMDGEDFQLS
mHIF-1α        DLDLEMLAPYIPMD-DDFQLR
mHIF-2α        ELDLETLAPYIPMDGEDFQLS
mHIF-3α        TLDLEMLAPYISMD-DDFQLN
xHIF-1α        DLDLEMLAPYIPMD-DDFQLR
dSIM           FEAFAMRAPYIPID-DDMPLL
C.eleg HIF     EPDLSQLAPFVDTY-DMMQM
```

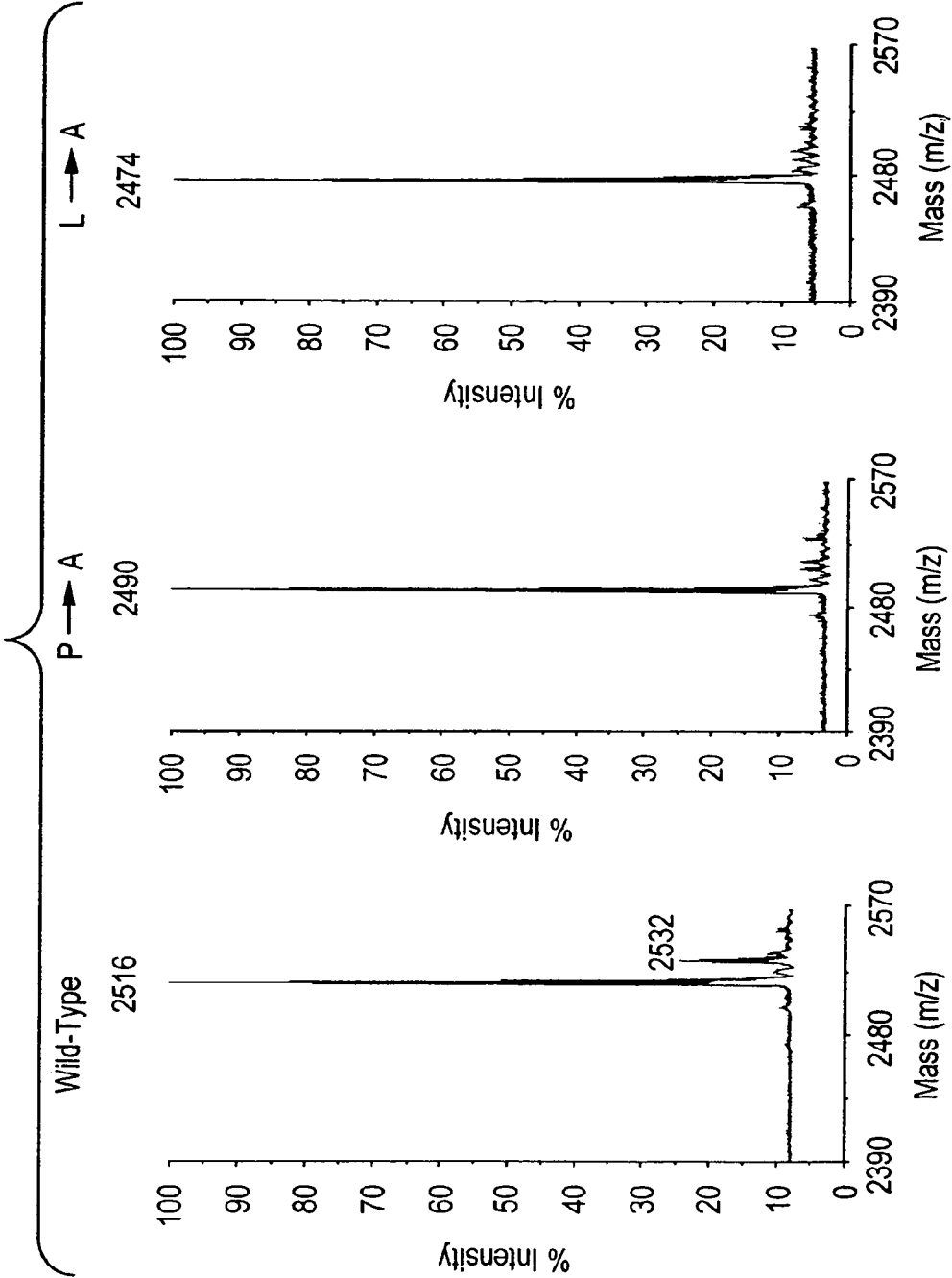

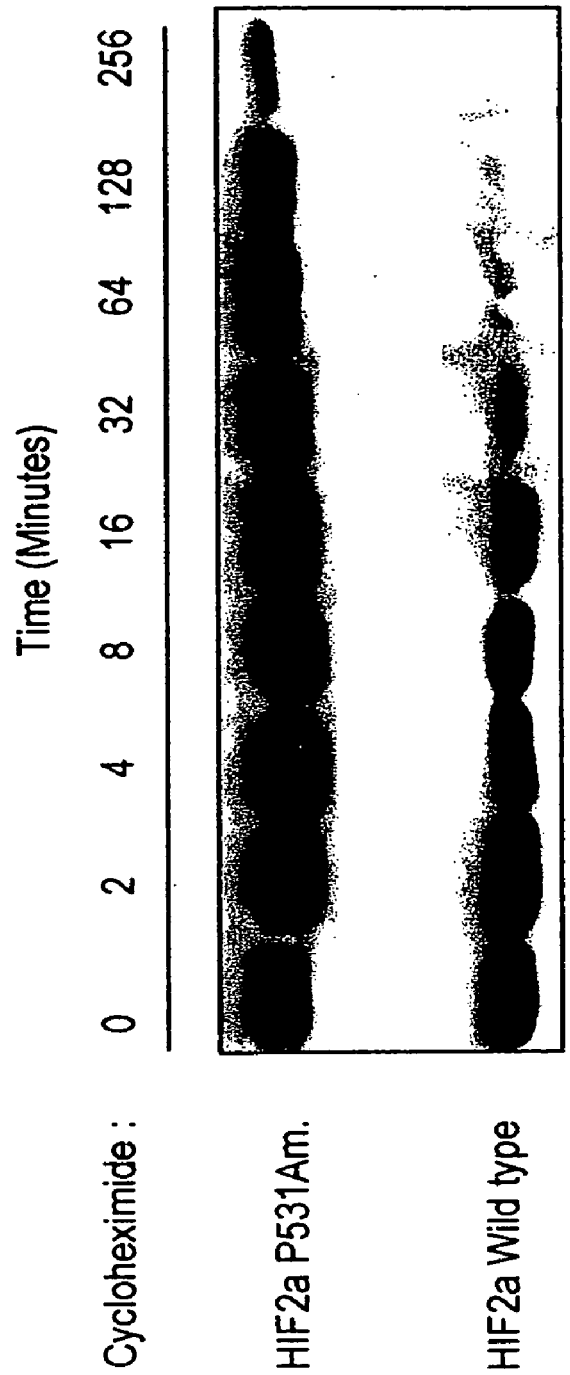

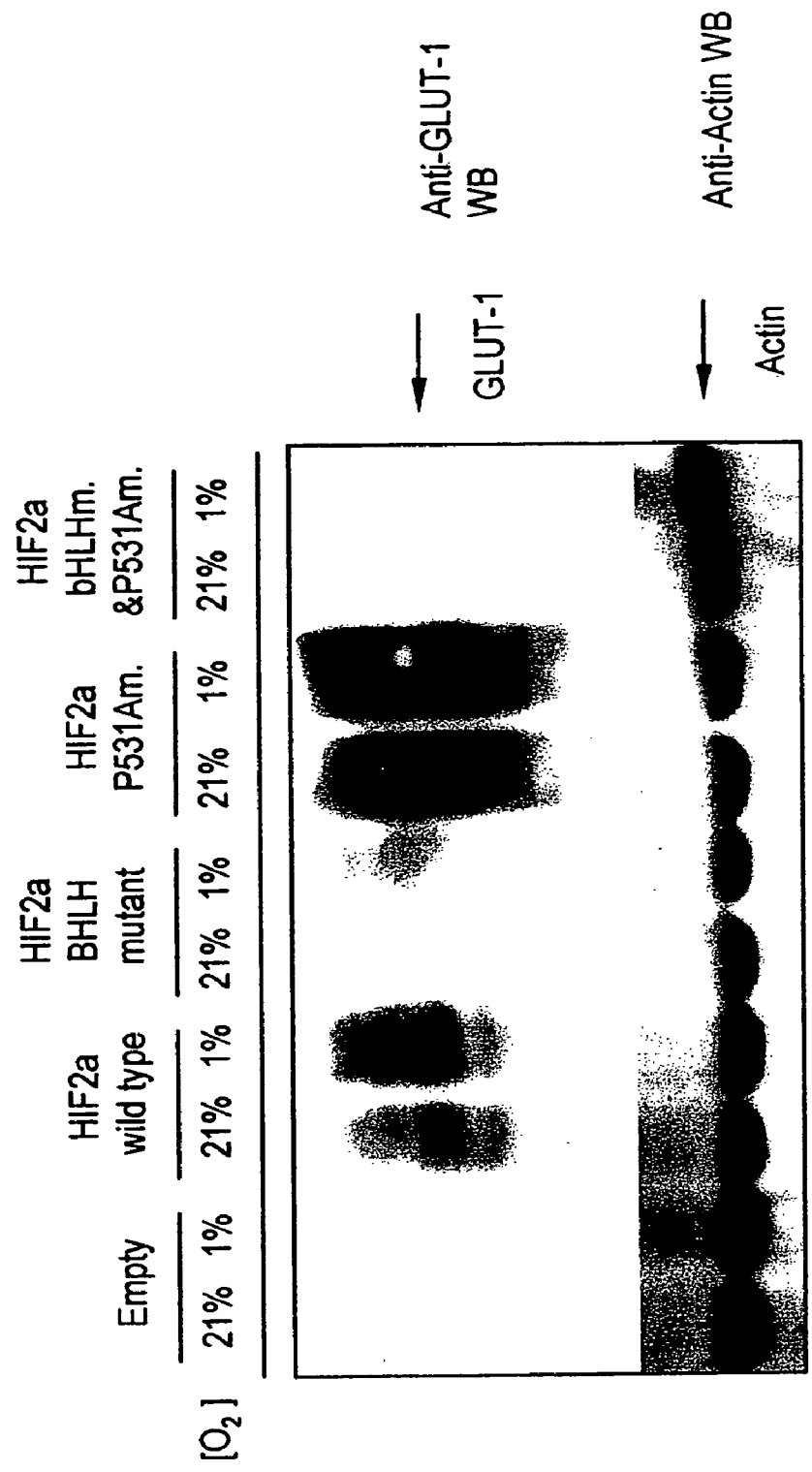

FIG. 8

```
atggagggcgccggcggcgcgaacgacaagaaaaagataagttctgaacgtcgaaaagaaaagtctcgaga
tgcagccagatctcggcgaagtaaagaatctgaagttttttatgagcttgctcatcagttgccacttccac
ataatgtgagttcgcatcttgataaggcctctgtgatgaggcttaccatcagctatttgcgtgtgaggaaa
cttctggatgctggtgatttggatattgaagatgacatgaaagcacagatgaattgcttttatttgaaagc
cttggatggttttgttatggttctcacagatgatggtgacatgatttacatttctgataatgtgaacaaat
acatgggattaactcagtttgaactaactggacacagtgtgtttgattttactcatccatgtgaccatgag
gaaatgagagaaatgcttacacacagaaatggccttgtgaaaagggtaaagaacaaaacacacagcgaag
cttttttctcagaatgaagtgtaccctaactagccgaggaagaactatgaacataaagtctgcaacatgga
aggtattgcactgcacaggccacattcacgtatatgataccaacagtaaccaacctcagtgtgggtataag
aaaccacctatgacctgcttggtgctgatttgtgaacccattcctcacccatcaaatattgaaattcctttt
agatagcaagactttcctcagtcgacacagcctggatatgaaattttcttattgtgatgaaagaattaccg
aattgatgggatatgagccagaagaacttttaggccgctcaatttatgaatattatcatgctttggactct
gatcatctgaccaaaactcatcatgatatgttttactaaaggacaagtcaccacaggacagtacaggatgct
tgccaaaagaggtggatatgtctggggttgaaactcaagcaactgtcatatataacaccaagaattctcaac
cacagtgcattgtatgtgtgaattacgttgtgagtggtattattcagcacgacttgatttctcccttcaa
caaacagaatgtgtccttaaaccggttgaatcttcagatatgaaaatgactcagctattcaccaaagttga
atcagaagatacaagtagcctctttgacaaacttaagaaggaacctgatgctttaactttgctggccccag
ccgctggagacacaatcatatctttagattttggcagcaacgacacagaaactgatgaccagcaacttgag
gaagtaccattatataatgatgtaatgctcccctcacccaacgaaaaattacagaatataaatttggcaat
gtctccattacccaccgctgaaacgccaaagccacttcgaagtagtgctgaccctgcactcaatcaagaag
ttgcattaaaattagaaccaaatccagagtcactggaactttcttttaccatgccccagattcaggatcag
acacctagtccttccgatggaagcactagacaaagttcacctgagcctaatagtcccagtgaatattgttt
ttatgtggatagtgatatggtcaatgaattcaagttggaattggtagaaaaacttttttgctgaagacacag
aagcaaagaacccattttctactcaggacacagatttagacttggagatgttagctgcttatatcccaatg
gatgatgacttccagttacgttccttcgatcagttgtcaccattagaaagcagttccgcaagccctgaaag
cgcaagtcctcaaagcacagttacagtattccagcagactcaaatacaagaacctactgctaatgccacca
ctaccactgccaccactgatgaattaaaaacagtgacaaaagaccgtatggaagacattaaaatattgatt
gcatctccatctcctacccacatacataaagaaactactagtgccacatcatccacatatagagatactca
aagtcggacagcctccaccaaacagagcaggaaaaggagtcatagaacagacagaaaaatctcatccaagaa
gccctaacgtgttatctgtcgctttgagtcaaagaactacagttcctgaggaagaactaaatccaaagata
ctagctttgcagaatgctcagagaaagcgaaaaatggaacatgatggttcacttttcaagcagtaggaat
tggaacattattacagcagccagacgatcatgcagctactacatcactttcttggaaacgtgtaaaaggat
gcaaatctagtgaacagaatggaatggagcaaaagacaattatttttaatacctctgatttagcatgtaga
ctgctggggcaatcaatggatgaaagtggattaccacagctgaccagttatgattgtgaagttaatgctcc
tatacaaggcagcagaaacctactgcagggtgaagaattactcagagctttggatcaagttaactga
(SEQ ID NO:1)
```

MEGAGGANDKKKISSERRKEKSRDAARSRRSKESEVFYELAHQLPLPHNVSSHLDKASVMRLTISYLRVRK
LLDAGDLDIEDDMKAQMNCFYLKALDGFVMVLTDDGDMIYISDNVNKYMGLTQFELTGHSVFDFTHPCDHE
EMREMLTHRNGLVKKGKEQNTQRSFFLRMKCTLTSRGRTMNIKSATWKVLHCTGHIHVYDTNSNQPQCGYK
KPPMTCLVLICEPIPHPSNIEIPLDSKTFLSRHSLDMKFSYCDERITELMGYEPEELLGRSIYEYYHALDS
DHLTKTHHDMFTKGQVTTGQYRMLAKRGGYVWVETQATVIYNTKNSQPQCIVCVNYVVSGIIQHDLIFSLQ
QTECVLKPVESSDMKMTQLFTKVESEDTSSLFDKLKKEPDALTLLAPAAGDTIISLDFGSNDTETDDQQLE
EVPLYNDVMLPSPNEKLQNINLAMSPLPTAETPKPLRSSADPALNQEVALKLEPNPESLELSFTMPQIQDQ
TPSPSDGSTRQSSPEPNSPSEYCFYVDSDMVNEFKLELVEKLFAEDTEAKNPFSTQDTDLDLEMLAAYIPM
DDDFQLRSFDQLSPLESSSASPESASPQSTVTVFQQTQIQEPTANATTTTATTDELKTVTKDRMEDIKILI
ASPSPTHIHKETTSATSSPYRDTQSRTASPNRAGKGVIEQTEKSHPRSPNVLSVALSQRTTVPEEELNPKI
LALQNAQRKRKMEHDGSLFQAVGIGTLLQQPDDHAATTSLSWKRVKGCKSSEQNGMEQKTIILIPSDLACR
LLGQSMDESGLPQLTSYDCEVNAPIQGSRNLLQGEELLRALDQVN (SEQ ID NO:2)

FIG. 9

```
atgacagctgacaaggagaagaaaaggagtagctcggagaggaggaaggagaagtcccgggatgctgcgcg
gtgccggcggagcaaggagacggaggtgttctatgagctggcccatgagctgcctctgccccacagtgtga
gctcccatctggacaaggcctccatcatgcgactggcaatcagcttcctgcgaacacacaagctcctctcc
tcagtttgctctgaaaacgagtccgaagccgaagctgaccagcagatggacaacttgtacctgaaagcctt
ggagggtttcattgccgtggtgacccaagatggcgacatgatctttctgtcagaaaacatcagcaagttca
tgggacttacacaggtggagctaacaggacatagtatctttgacttcactcatccctgcgaccatgaggag
attcgtgagaacctgagtctcaaaaatggctctggttttgggaaaaaaagcaaagacatgtccacagagcg
ggacttcttcatgaggatgaagtgcacggtcaccaacagaggccgtactgtcaacctcaagtcagccacct
ggaaggtcttgcactgcacgggccaggtgaaagtctacaacaactgccctcctcacaatagtctgtgtggc
tacaaggagcccctgctgtcctgcctcatcatcatgtgtgaaccaatccagcacccatcccacatggacat
ccccctggatagcaagaccttcctgagccgccacagcatggacatgaagttcacctactgtgatgacagaa
tcacagaactgattggttaccaccctgaggagctgcttggccgctcagcctatgaattctaccatgcgcta
gactccgagaacatgaccaagagtcaccagaacttgtgcaccaagggtcaggtagtaagtggccagtaccg
gatgctcgcaaagcatggggggctacgtgtggctggagacccaggggacggtcatctacaaccctcgcaacc
tgcagccccagtgcatcatgtgtgtcaactacgtcctgagtgagattgagaagaatgacgtggtgttctcc
atggaccagactgaatccctgttcaagccccacctgatggccatgaacagcatctttgatagcagtggcaa
ggggggctgtgtctgagaagagtaacttcctattcaccaagctaaaggaggagcccgaggagctggcccagc
tggctcccaccccaggagacgccatcatctctctggatttcgggaatcagaacttcgaggagtcctcagcc
tatggcaaggccatcctgccccgagccagccatgggccacggagttgaggagccacagcacccagagcga
ggctgggagcctgcctgccttcaccgtgccccaggcagctgccccgggcagcaccacccccagtgccacca
gcagcagcagcagctgctccacgcccaatagccctgaagactattacacatctttggataacgacctgaag
attgaagtgattgagaagctcttcgccatggacacagaggccaaggaccaatgcagtacccagacggattt
caatgagctggacttggagacactggcagcttatatccccatggacggggaaggcttccagctaagcccca
tctgccccgaggagcggctcttggcggagaaccacagtccaccccccagcactgcttcagtgccatgaca
aacatcttccagccactggccctgtagccccggcccagtccttcctcctggacaagtttcagcagcagct
ggagagcaagaagacagagcccgagcgccggcccatgtcctccatcttctttgatgccggaagcaaagcat
ccctgccaccgtgctgtggccaggccagcacccctctctcttccatgggggggcagatccaacacccagtgg
cccccagatccaccattacattttgggcccacaaagtgggccgtcggggatcagcgcacagagttcttggg
agcagcgccgttggggcccctgtctctccaccccatgtctccaccttcaaaacaaggtctgcaaaggggtt
ttggggctcgaggcccaaacgtgctgagtccggccatggtagccctctccaacaagctgaagctgaagcga
cagctggagtatgaaaagcaagccttccaggacccgagcgggggggacccacctggtggcagcacctcaca
tttgatgtggaaacggatgaagaacctcaggggtgggagctgccctttgatgccggacaagccactgagcg
caaatgtacccaatgataagctcacccaaaactccatgaggggcctggccatcccctgagacatctgccg
ctgccacagcctccatctgccatcagtcccggggagaacagcaagagcaggttcccccccacagtgctacgc
cacccagtaccaggactacagcctgtcgtcagcccacaaggtgtcaggcatggcaagccggctgctcgggc
cctcatttgagtcctacctgctgcccgaactgaccagatatgaccgtgaggtgaaagtgcccgtgctggga
agctccacgctcctgcaaggaggggacctcctcagagccctggaccaggccacctga (SEQ ID NO:3)
```

```
MTADKEKKRSSSERRKEKSRDAARCRRSKETEVFYELAHELPLPHSVSSHLDKASIMRLAISFLRTHKLLS
SVCSENESEAEADQQMDNLYLKALEGFIAVVTQDGDMIFLSENISKFMGLTQVELTGHSIFDFTHPCDHEE
IRENLSLKNGSGFGKKSKDMSTERDFFMRMKCTVTNRGRTVNLKSATWKVLHCTGQVKVYNNCPPHNSLCG
YKEPLLSCLIIMCEPIQHPSHMDIPLDSKTFLSRHSMDMKFTYCDDRITELIGYHPEELLGRSAYEFYHAL
DSENMTKSHQNLCTKGQVVSGQYRMLAKHGGYVWLETQGTVIYNPRNLQPQCIMCVNYVLSEIEKNDVVFS
MDQTESLFKPHLMAMNSIFDSSGKGAVSEKSNFLFTKLKEEPEELAQLAPTPGDAIISLDFGNQNFEESSA
YGKAILPPSQPWATELRSHSTQSEAGSLPAFTVPQAAAPGSTTPSATSSSSSCSTPNSPEDYYTSLDNDLK
IEVIEKLFAMDTEAKDQCSTQTDFNELDLETLAAYIPMDGEGFQLSPICPEERLLAENPQSTPQHCFSAMT
NIFQPLAPVAPHSPFLLDKFQQQLESKKTEPERRPMSSIFFDAGSKASLPPCCGQASTPLSSMGGRSNTQW
PPDPPLHFGPTKWAVGDQRTEFLGAAPLGPPVSPPHVSTFKTRSAKGFGARGPNVLSPAMVALSNKLKLKR
QLEYEKQAFQDPSGGDPPGGSTSHLMWKRMKNLRGGSCPLMPDKPLSANVPNDKLTQNSMRGLGHPLRHLP
LPQPPSAISPGENSKSRFPPQCYATQYQDYSLSSAHKVSGMASRLLGPSFESYLLPELTRYDREVKVPVLG
SSTLLQGGDLLRALDQAT (SEQ ID NO:4)
```

MUTEINS OF HYPOXIA INDUCIBLE FACTOR ALPHA AND METHODS OF USE THEREOF

RELATED APPLICATIONS

This application is a continuation of U.S. Ser. No. 10/101,816, filed Mar. 19, 2002, now U.S. Pat. No. 6,849,718, which claims priority to U.S. Application Nos. 60/277,425, filed Mar. 20, 2001; 60/277,431, filed Mar. 20, 2001; 60/277,440, filed Mar. 20, 2001; 60/332,493, filed Nov. 9, 2001; 60/332, 334, filed Nov. 9, 2001; 60/345,200, filed Nov. 9, 2001; 60/345,131 filed Dec. 20, 2001, 60/342,598, filed Dec. 20, 2001; and 60/345,132, filed Dec. 20, 2001 each of which are incorporated herein by reference in their entireties.

FIELD OF THE INVENTION

The invention relates to polypeptides and nucleic acids encoding hypoxia inducible factor muteins.

BACKGROUND OF THE INVENTION

Mammals require molecular oxygen ($O_2$) for essential metabolic processes including oxidative phosphorylation in which $O_2$ serves as electron acceptor during ATP formation. Systemic, local, and intracellular homeostatic responses elicited by hypoxia (the state in which $O_2$ demand exceeds supply) include erythropoiesis by individuals who are anemic or at high altitude (Jelkmann, *Physiol. Rev.* 72:449–489, 1992), neovascularization in ischemic myocardium (White et al., *Circ. Res.* 71:1490–1500, 1992), and glycolysis in cells cultured at reduced $O_2$ tension (Wolfe et al., *Eur. J. Biochem.* 135:405–412, 1983). These adaptive responses either increase $O_2$ delivery or activate alternate metabolic pathways that do not require $O_2$. Hypoxia-inducible gene products that participate in these responses include erythropoietin (EPO) (reviewed in Semenza, *Hematol. Oncol. Clinics N. Amer.* 8:863–884, 1994), vascular endothelial growth factor (VEGF) (Skweiki et al., *Nature* 359:843–845, 1992; Banai et al., *Cardiovasc. Res.* 28:1176–1179, 1994; Goldberg & Schneider, *J. Biol. Chem.* 269:4355–4359, 1994), and glycolytic enzymes (Firth et al., *Proc. Natl. Acad. Sci. USA* 91:6496–6500, 1994; Semenza et al., *J. Biol. Chem.* 269:23757–23763, 1994).

The molecular mechanisms that mediate genetic responses to hypoxia have been extensively investigated for the EPO gene, which encodes a growth factor that regulates erythropoiesis and thus blood $O_2$-carrying capacity (Jelkmann, 1992, supra; Semenza, 1994, supra). Cis-acting DNA sequences required for transcriptional activation in response to hypoxia were identified in the EPO 3'-flanking region and a trans-acting factor that binds to the enhancer, hypoxia-inducible factor 1 (HIF-1), fulfilled criteria for a physiological regulator of EPO transcription. In particular, inducers of EPO expression (1% $O_2$, cobalt chloride [$CoCl_2$], and desferrioxamine [DFX]) also induced HIF-1 DNA binding activity with similar kinetics. In addition, inhibitors of EPO expression (actinomycin D, cycloheximide, and 2-aminopurine) blocked induction of HIF-1 activity. Furthermore, mutations in the EPO 3'-flanking region that eliminated HIF-1 binding also eliminated enhancer function (Semenza, 1994, supra). These results support a signal transduction pathway requiring ongoing transcription, translation, and protein phosphorylation in the induction of HIF-1 DNA-binding activity and EPO transcription in hypoxic cells (Semenza, 1994, supra).

EPO expression is cell type specific, but induction of HIF-1 activity by 1% $O_2$ $CoCl_2$, or DFX was detected in many mammalian cell lines (Wang & Semenza, *Proc. Natl. Acad. Sci. USA* 90:4304–4308, 1993). The EPO enhancer directed hypoxia-inducible transcription of reporter genes transfected into non-EPO-producing cells (Wang & Sernenza, 1993, supra; Maxwell et al., *Proc. Natl. Acad. Sci. USA* 90:2423–2427, 1993). RNAs encoding several glycolytic enzymes were induced by 1% $O_2$, $CoCl_2$, or DFX in EPO-producing Hep3B or nonproducing HeLa cells whereas cycloheximide blocked their induction and glycolytic gene sequences containing HIF-1 binding sites mediated hypoxia-inducible transcription in transfection assays (Firth et al., 1994, supra; Semenza et al., 1994, supra). These experiments support the role of HIF-1 in activating homeostatic responses to hypoxia.

Hypoxia inducible factor-1(HIF-1) is a mammalian transcription factor expressed uniquely in response to physiologically relevant levels of hypoxia (Wang, G. L., et al., *Proc. Natl. Acad. Sci. USA* 92:5510–5514, 1995; Wang, G. L., and Semenza, G. L., *J. Biol. Chem.* 270:1230–1237, 1995; U.S. Pat. No. 5,882,914). HIF-1 is a basic helix loop-helix protein that binds to cis-acting hypoxia-responsive elements of genes induced by hypoxia (Wang, G. L., and Semenza, G. L., *Curr. Opin. Hematol.* 3:156–162, 1992; Jiang, B. H., et al., *J. Biol. Chem.* 272:19253–19260, 1997). The genes that are activated by HIF-1 in cells subjected to hypoxia include EPO, vascular endothelial growth hormone (VEGF), heme oxygenase-1, inducible nitric oxide synthase, and glycolytic enzymes aldolase A, enolase 1, lactate dehydrogenase A, phosphofructokinase I, and phosphoglycerate kinase 1 (Semenza, G. L., et al., *Kid. Int.* 51:553–555, 1997). HIF-1 DNA binding activity and HIF-1 protein concentration increase exponentially as cells are subjected to decreasing $O_2$ concentrations (Jiang, B. H., et al., *Am J. Physiol.* 271:C1172–C1180, 1996).

HIF-1 also activates transcription of the VEGF gene in hypoxic cells (Forsythe et al., 1996; Iyer et al., 1998). When cultured cells are transfected with pCEP4/HIF-1alpha plasmid under conditions that allow expression of HIF-1alpha from a cytomegalovirus promoter and a reporter plasmid containing the hypoxia response element from the VEGF gene, reporter gene expression is increased in cells under non-hypoxic conditions and there is a dramatic superinduction under hypoxic conditions that is dependent upon the presence of an intact HIF-1 binding site (Forsythe et al., 1996). In embryonic stem cells from a knockout mouse, which lack HIF-1alpha expression, there is no expression of VEGF mRNA in response to hypoxia (Iyer et al., 1998).

HIF-1 is a heterodimer of two subunits, HIF-1alpha and HIF-1beta. The HIF-1alpha subunit is unique to HIF-1, whereas HIF-1 beta (also known as aryl hydrocarbon receptor nuclear translocator, ARNT) can dimerize with other proteins. HIF-1 alpha-subunits are stabilized under hypoxic conditions and are important in regulating genes involved in angiogenesis and glucose metabolism.

Structural analysis of HIF-1alpha revealed that dimerization requires two domains, termed HLH and PAS. DNA binding is mediated by a basic domain (Semenza, G. L., et al., *Kid. Int.* 51:553–555, 1997). Two transactivation domains are contained in HIF-1alpha, located between amino acids 531 and 826. The minimal transactivation domains are at amino acid residues 531–575 and 786–826 (Jiang, B. H., et al., 1997, supra; Semenza, G. L., et al., 1997, supra). Amino acids 1–390 are required for optimal heterodimerization with HIF1beta (ARNT) and DNA binding. In addition, deletion of the carboxy terminus of HIF-1alpha (amino acids 391–826) decreased the ability of HIF-1 to activate transcription. However, HIF-1alpha (1–390) was expressed at high levels in both hypoxic and non-hypoxic cells in contrast to full-length HIF-1 alpha (1–826) which was expressed at much higher levels in hypoxic relative to non-hypoxic cells (Jiang, B.-H., et al., *J. Biol. Chem.* 271: 17771–17778, 1996). Thus, hypoxia has two independent effects on HIF-1alpha activity: (1) hypoxia increases the steady-state levels of HIF-1alpha protein by stabilizing it (i.e. decreasing its degradation); and (2) hypoxia increases the specific transcriptional activity of the protein (i.e. independent of the protein concentration).

SUMMARY OF THE INVENTION

The invention provides hypoxia inducible factor (HIF) mutein polypeptides. In one aspect a HIF mutein polypeptide includes a polypeptide where one or more of a hydroxylatable amino acid residue in a wild type HIFα polypeptide are mutated. These mutations result in a HIF mutein displaying decreased binding to VHL, increased resistance to degradation in the presence of oxygen and has both functional wild type HIFα polypeptide transactivation domains.

In a further aspect the invention provides hypoxia inducible factor (HIF) mutein polypeptides where a wild-type HIF alpha polypeptide and polypeptides 85% similar to wild-type-HIF have one or more amino acid mutations. These mutations result in a HIF mutein that has decreased binding to Von Hippel-Lindau (VHL) polypeptide and increased resistance to degradation in the presence of oxygen. These mutations include, for example, a mutation at amino acid position 564, numbered in accordance with wild type HIFα where the amino acid is not is not a proline. Alternatively, the amino acid at position 562 is not a leucine. In another aspect, the amino acid at position 402, in a HIF mutein polypeptide is not a proline. Preferably, the amino acid at position, 564, 562 or 402 are alanine.

In one aspect the HIF mutein includes the sequence of SEQ ID NO:2 or SEQ ID NO:4.

The invention also provides nucleic acids encoding HIF mutein, for example SEQ ID NO:1, recombinant DNA molecules containing those sequences operatively linked to expression control sequences and capable of inducing, in an appropriate host, the expression of the HIF muteins, hosts transformed with those recombinant DNA molecules, HIF mutein antibodies and pharmaceutical compositions containing the HIF muteins. These compositions are useful in treating or preventing hypoxia and ischemica related tissue damage and modulating angiogenesis or vascularization.

In a further aspect the invention provide a method for increasing the expression of at least one gene in a cell whose expression is activated by a HIF polypeptide by contacting the cell with a HIF mutein nucleic acid, e.g., an expression vector containing a HIF nucleic acid. The cell can be contacted in vivo, in vitro or ex vivo.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 2E. is an illustration depicting the conservation of Leu562 and Pro564 among HIF orthologs and paralogs.

FIG. 4A is an illustration MALDI-TOF analysis of wild-type, Pro564Ala, and Leu562Ala biotinylated HIF (556–575)peptides following incubation with rabbit reticulocyte lysate

FIG. 6 is a photograph of a blot demonstrating the stability of HIF2alpha wild type and P531A mutant in WT8 (VHL positve) renal carcinoma WT8 cells. WT8 stably infected with Hemaggulutinin (HA) tagged HIF2α wild type and P531 A mutant were incubated with cycloheximide. At the indicated timepoints thereafter cell extracts were prepared and analyzed by anti-HA immunoblot assay. Each lane contained 100 microgram of protein extract.

FIG. 7 is a photograph of a blot demonstrating the Glut-1 induction by HIF2α wild type and mutants. WT8 (VHL positive) renal carcinoma cells were stably infected with an empty retrovirus or retroviruses encoding hemaggulutinin (HA)-tagged HIF2alpha wild-type, HIF2alpha basic helix-loop-helix (bHLH) mutant, HIF2alpha P531A mutant, or HIF2alpha basic helix-loop-helix/P531A double mutant. The cells were cultured under normoxic (21%) and hypoxic (1%) conditions for 12 hrs, lysed, and immunoblotted with antibodies against GLUT. 50 ug of whole cell extract was loaded in each lane and comparable loading was confirmed by anti-actin western blot analysis.

FIG. 8 is an illustration depicting the nucleic acid (SEQ ID NO:1) and encoded polypeptide (SEQ ID NO:2) sequence of a HIF mutein according to the invention.

FIG. 9 is an illustration depicting the nucleic acid (SEQ ID NO:3) and encoded polypeptide (SEQ ID NO:4) sequence of a HIF mutein according to the invention.

DETAILED DESCRIPTION OF THE INVENTION

Figure 1C:
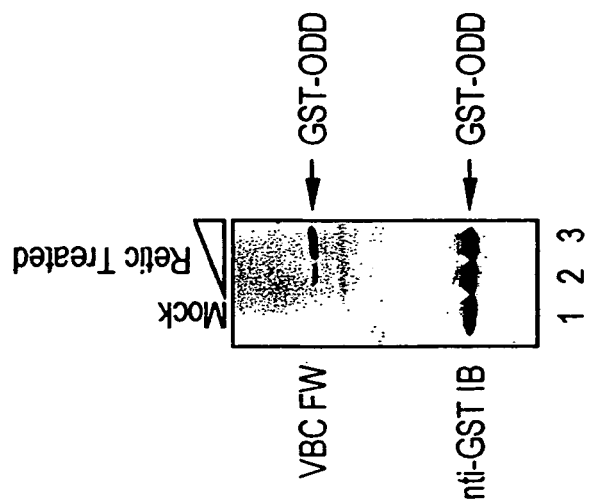
FIG. 1C. is a photograph of a blot showing that pVHL binds to a modified form of HIF. GST-HIF1α(530–652), containing the oxygen-dependent degradation domain (ODD), was produced in *E. Coli*, recovered on glutathione sepharose, and incubated with rabbit reticulocyte lysate for 90 min at 30° C. After stringent washes the GST-ODD protein was subjected to VBC farwestern and anti-GST immunoblot analysis.

The invention provides stable hypoxia-inducible factor alpha (HIF alpha) proteins, or muteins and nucleic acids. The nucleic acid sequences and polypeptides of the present invention are herein referred to as, sHIF proteins or polypeptides or a HIF mutein.

As used herein, "wild type HIF-alpha" means an wild type HIF-alpha (i.e., HIF-1alpha, HIF-2 alpha or HIF-3 alpha), whether native or recombinant, having the normally occurring amino acid sequence of native HIF-alpha, as shown in, e.g., GenBank Accession Nos: BAB70608, BAB69689, BAA34234 or AAP24413.

Wild-type, full-length HIF-alpha is expressed at lower levels in nonhypoxic cells as compared to hypoxic cells (Wang, G. L., et al., *Proc. Natl. Acad. Sci. USA* 92:5510–5514, 1995; Wang, G. L., and Semenza, G. L., *J. Biol. Chem.* 270:1230–1237, 1995; Jiang, B. H., et al., *J. Biol. Chem.* 272:19253–19260, 1997, herein incorporated by reference). Wild type HIF-alpha is characterized as being able to form heterodimers with HIF-beta to form a DNA-binding protein, hypoxia inducible factor (HIF), a mammalian transcription factor. HIF activates transcription of multiple genes including those encoding erythropoietin (EPO), vascular endothelial growth factor (VEGF), glucose transporters, and glycolytic enzymes.

The term "mutein" as used herein refers to a variant form of HIF alpha polypeptide that is stable under hypoxic or non-hypoxic conditions. By "stable" it is meant that the HIF mutein is more resistant to degredation compared (i.e., an increased half-life as compared to wild-type HIF-alpha under nonhypoxic conditions to wild-type HIF-alpha.) Hypoxia is a condition where the oxygen demand in a tissue exceeds the supply of oxygen in that tissue. The terms "hypoxic" and "non-hypoxic" are understood to be relative terms with respect to oxygen concentration typically observed in a particular tissue. In addition, a HIF mutein displays decreased binding to von Hippel-Lindau (VHL) proteins.

sHIF Polypeptides

A HIF mutein polypeptide includes a polypeptide where one or more of a hydroxylatable amino acid residue in a wild type HIFα polypeptide are mutated. Alternatively, a HIF mutein includes a polypeptides where on or more amino acids residues in a wild type HIF are mutated such to inhibit hydroxylation of the polypeptide. These mutations result in a HIF mutein displaying decreased binding to VHL, increased resistance to degradation in the presence of oxygen and has both functional wild type HIFα polypeptide transactivation domains. By "hydroxylatable" is meant that the amino acid residue is capable of being hydroxylated. An example of an hydroxylatable amino acid residue is proline.

By "functional wild type HIFα polypeptide transactivation domains" is meant that the HIF mutein retains the transactivating function of wild type HIFα. For example the HIF mutein is capable of activating transcription of erythropoietin (EPO), vascular endothelial growth factor (VEGF), glucose transporters, and glycolytic enzymes. Wild type HIFα activates transcription of hypoxia inducible genes via two highly conserved transctivation domais in the C-terminal half of the polypeptide. These two domains have been designated as NAD (N-terminal activation domain) which comprise amino acids 481–603 and CAD (C-terminal activation domain) which comprises amino acid residues 776–826. NADs, which were rarely detectable at normoxia, are stabilized and accumulated at hypoxia, whereas CADs were constitutively expressed.

A HIF mutein, includes a polypeptide where the amino acid at position 564 is not a proline when numbered in accordance with wild type HIF-alpha. Alternatively, a HIF mutein includes a polypeptide where the amino acid at position 562 is not a leucine. Preferably, a HIF mutein includes a polypeptide where the amino acids at position 564 is not a proline and amino acid at 562 is not a leucine. Preferably, the amino acids at positions 564 and/or 562 is alanine. In addition, a HIF mutein includes a polypeptide where the amino acid at position 402 is not a proline.

A sHIF polypeptide of the invention includes for example, the protein whose sequence is provided in SEQ ID NO:2 or SEQ ID NO: 4. The invention also includes a mutant or variant protein any of whose residues may be changed from the corresponding residue shown in SEQ ID NO:2 or SEQ ID NO:4 while still encoding a protein that maintains its sHIF-like activities and physiological functions, or a functional fragment thereof. In some embodiments, up to 20% or more of the residues may be so changed in the mutant or variant protein. Preferably, the HIF mutein is at least about 80% homologous to wild-type HIF alpha, more preferably at least about 85%, 90%, 95%, 98%, and most preferably at least about 99% homologous to wild-type HIF alpha. In general, a sHIF-like variant that preserves sHIF-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above. sHIF like activities include, for example, stablility under hypoxic or nonhypoxic condition, decreased binding toVHL, reducing hypoxia or ischemia-related tissue damage, or modulating angiogenesis.

Minor modifications of the sHIF primary amino acid sequence may result in proteins which are stable under nonhypoxic conditions and have substantially equivalent activity as compared to the sHIF alpha polypeptide described herein. These minor modifications include the minor differences found in the sequence of HIF-alpha polypeptide isolated from different species (e.g., human, mouse, and rat HIF alpha polypeptide). Such proteins include those as defined by the term "having essentially the amino acid sequence" of the sHIF alpha of the invention. Such modifications may be deliberate, as by site-directed mutagenesis, or may be spontaneous, as those found in different species. All of the polypeptides produced by these modifications are included herein as long as the biological activity of sHIF-slphs still exists, and the polypeptide is stable under nonhypoxic conditions as compared to wild-type HIF-alpha. Further, deletions of one or more amino acids can also result in modification of the structure of the resultant molecule without significantly altering its biological activity. For example, one can remove amino or carboxy terminal amino acids which are not required for sHIF alpha biological activity.

One aspect of the invention pertains to isolated sHIF proteins, and biologically active portions thereof, or derivatives, fragments, analogs or analogs thereof. Also provided are polypeptide fragments suitable for use as immunogens to raise anti-sHIF antibodies.

sHIF polypeptides are easily prepared using modern cloning techniques, or may be synthesized by solid state methods by site-directed mutagenesis. A sHIF polypeptide may include dominant negative forms of a polypeptide. In one embodiment, native sHIF proteins can be isolated from cells or tissue sources by an appropriate purification scheme using standard protein purification techniques. In another embodiment, sHIF proteins are produced by recombinant DNA techniques. Alternative to recombinant expression, a sHIF protein or polypeptide can be synthesized chemically using standard peptide synthesis techniques.

An "isolated" or "purified" protein or biologically active portion thereof is substantially free of cellular material or other contaminating proteins from the cell or tissue source from which the sHIF protein is derived, or substantially free from chemical precursors or other chemicals when chemically synthesized. The language "substantially free of cellular material" includes preparations of sHIF protein in which the protein is separated from cellular components of the cells from which it is isolated or recombinantly produced. In one embodiment, the language "substantially free of cellular material" includes preparations of sHIF protein having less than about 30% (by dry weight) of non-sHIF protein (also referred to herein as a "contaminating protein"), more preferably less than about 20% of non-sHIF protein, still more preferably less than about 10% of non-sHIF protein, and most preferably less than about 5% non-sHIF protein. When the sHIF protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of sHIF protein in which the protein is separated from chemical precursors or other chemicals that are involved in the synthesis of the protein. In one embodiment, the language "substantially free of chemical precursors or other chemicals" includes preparations of sHIF protein having less than about 30% (by dry weight) of chemical precursors or non-sHIF chemicals, more preferably less than about 20% chemical precursors or non-sHIF chemicals, still more preferably less than about 10% chemical precursors or non-sHIF chemicals, and most preferably less than about 5% chemical precursors or non-sHIF chemicals.

Biologically active portions of a sHIF protein include peptides comprising amino acid sequences sufficiently homologous to or derived from the amino acid sequence of the sHIF protein, e.g., the amino acid sequence shown in SEQ ID NO:2 or SEQ ID NO:4 that include fewer amino acids than the full length sHIF proteins, and exhibit at least one activity of a sHIF protein. Typically, biologically active portions comprise a domain or motif with at least one activity of the sHIF protein. A biologically active portion of a sHIF protein can be a polypeptide which is, for example, 10, 25, 50, 100 or more amino acids in length.

A biologically active portion of a sHIF protein of the present invention may contain at least one of the above-identified domains conserved between the sHIF proteins, e.g. oxygen dependent degradation domain (ODD). Moreover, other biologically active portions, in which other regions of the protein are deleted, can be prepared by recombinant techniques and evaluated for one or more of the functional activities of a native sHIF protein.

sHIF Chimeric and Fusion Proteins

The invention also provides sHIF chimeric or fusion proteins. As used herein, a sHIF "chimeric protein" or "fusion protein" comprises a sHIF polypeptide operatively linked to a non-sHIF polypeptide. An "sHIF polypeptide" refers to a polypeptide having an amino acid sequence corresponding to sHIF, whereas a "non-sHIF polypeptide" refers to a polypeptide having an amino acid sequence corresponding to a protein that is not substantially homologous to the sHIF protein, e.g., a protein that is different from the sHIF protein and that is derived from the same or a different organism. Within a sHIF fusion protein the sHIF polypeptide can correspond to all or a portion of a sHIF protein. In one embodiment, a sHIF fusion protein comprises at least one biologically active portion of a HIF protein. In another embodiment, a sHIF fusion protein comprises at least two biologically active portions of a sHIF protein. Within the fusion protein, the term "operatively linked" is intended to indicate that the sHIF polypeptide and the non-sHIF polypeptide are fused in-frame to each other. The non-sHIF polypeptide can be fused to the N-terminus or C-terminus of the sHIF polypeptide.

For example, in one embodiment a sHIF fusion protein comprises a sHIF polypeptide operably linked to the extracellular domain of a second protein. Such fusion proteins can be further utilized in screening assays for compounds that modulate sHIF activity (such assays are described in detail below).

In another embodiment, the fusion protein is a GST-sHIF fusion protein in which the sHIF sequences are fused to the C-terminus of the GST (i.e., glutathione S-transferase) sequences. Such fusion proteins can facilitate the purification of recombinant sHIF.

A sHIF chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A sHIF-encoding nucleic acid can be cloned into such an expression vector such that the fusion moiety is linked in-frame to the sHIF protein.

sHIF Nucleic Acids

The nucleic acids of the invention include those that encode a sHIF polypeptide or protein. As used herein, the terms polypeptide and protein are interchangeable. These polynucleotides include DNA, cDNA, and RNA sequences which encode sHIF alpha. It is also understood that all polynucleotides encoding all or a portion of sHIF alpha are also included herein, as long as they encode a polypeptide with HIF-alpha activity which is stable under hypoxic and nonhypoxic conditions. Such polynucleotides include naturally occurring, synthetic, and intentionally manipulated polynucleotides. For example, sHIF polynucleotide may be subjected to site-directed mutagenesis. The polynucleotide sequence for sHIF also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of HIF alpha polypeptide is encoded by the nucleotide sequence is functionally unchanged.

In some embodiments, a sHIF nucleic acid encodes a mature sHIF polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

Among the sHIF nucleic acids is the nucleic acid whose sequence is provided in SEQ ID NO: 1 or SEQ ID NO: 3, or a fragment thereof. Additionally, the invention includes mutant or variant nucleic acids of SEQ ID NO: 1 or SEQ ID NO: 3, or a fragment thereof, any of whose bases may be changed from the corresponding base shown in SEQ ID NO: 1 or SEQ ID NO: 3, while still encoding a protein that maintains at least one of its sHIF-like activities and physiological functions (i.e., stable under hypoxic and non-hypoxic conditions, reduced binding to VHL, reducincg hypoxia or ischemia-related tissue damage modulating angiogenesis). The invention further includes the complement of the nucleic acid sequence of SEQ ID NO: 1 or SEQ ID NO: 3, including fragments, derivatives, analogs and analogs thereof. The invention additionally includes nucleic acids or nucleic acid fragments, or complements thereto, whose structures include chemical modifications.

One aspect of the invention pertains to isolated nucleic acid molecules that encode sHIF proteins or biologically active portions thereof. Also included are nucleic acid fragments sufficient for use as hybridization probes to identify sHIF-encoding nucleic acids (e.g., sHIF mRNA) and fragments for use as polymerase chain reaction (PCR) primers for the amplification or mutation of sHIF nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated sHIF nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO: 1 or SEQ ID NO: 3, or a complement of any of this nucleotide sequence, can be isolated using standard molecular biology techniques and the sequence information provided herein. Using all or a portion of the nucleic acid sequence of SEQ ID NO: 1 or SEQ ID NO: 3 as a hybridization probe, sHIF nucleic acid sequences can be isolated using standard hybridization and cloning techniques (e.g., as described in Sambrook et al., eds., MOLECULAR CLONING: A LABORATORY MANUAL 2nd Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to sHIF nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO: 1 or SEQ ID NO: 3, or a complement thereof. Oligonucleotides may be chemically synthesized and may be used as probes.

In another embodiment, an isolated nucleic acid molecule of the invention includes a nucleic acid molecule that is a complement of the nucleotide sequence shown in SEQ ID NO: 1 or SEQ ID NO: 3. In another embodiment, an isolated nucleic acid molecule of the invention comprises a nucleic acid molecule that is a complement of the nucleotide sequence shown in SEQ ID NO: 1 or SEQ ID NO: 3, or a portion of this nucleotide sequence. A nucleic acid molecule that is complementary to the nucleotide sequence shown in SEQ ID NO: 1 or SEQ ID NO: 3 is one that is sufficiently complementary to the nucleotide sequence shown in SEQ ID NO: 1 or SEQ ID NO: 3 that it can hydrogen bond with little or no mismatches to the nucleotide sequence shown in SEQ ID NO: 1 or SEQ ID NO: 3, thereby forming a stable duplex.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the sHIF nucleic acid sequence, e.g., a fragment that can be used as a probe or primer, or a fragment encoding a biologically active portion of sHIF. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which is incorporated herein by reference in its entirety).

A "homologous nucleic acid sequence" or "homologous amino acid sequence," or variations thereof, refer to sequences characterized by a homology at the nucleotide level or amino acid level as discussed above. In the present invention, homologous nucleotide sequences include nucleotide sequences encoding for a sHIF polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. Homologous nucleic acid sequences include those nucleic acid sequences that encode conservative amino acid substitutions as well as a polypeptide having sHIF activity. Biological activities of the sHIF proteins are described above.

sHIF Variants

The invention further encompasses nucleic acid molecules that differ from the nucleotide sequences shown in SEQ ID NO: 1 or SEQ ID NO: 3 due to the degeneracy of the genetic code. These nucleic acids thus encode the same sHIF protein as that encoded by the nucleotide sequence shown in SEQ ID NO: 1 or SEQ ID NO: 3, e.g., the polypeptide of SEQ ID NO:2 or SEQ ID NO:4. In another embodiment, an isolated nucleic acid molecule of the invention has a nucleotide sequence encoding a protein having an amino acid sequence shown in SEQ ID NO:2 or SEQ ID NO:4

Moreover, nucleic acid molecules encoding sHIF proteins from other species, and thus that have a nucleotide sequence that differs from the human sequence of SEQ ID NO: 1 or SEQ ID NO: 3 are intended to be within the scope of the invention.

Homologs (i.e., nucleic acids encoding sHIF proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO: 1 or SEQ ID NO: 3 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO: 1 or SEQ ID NO: 3, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, N.Y.

In a third embodiment, a nucleic acid that is hybridizable to the nucleic acid molecule comprising the nucleotide sequence of SEQ ID NO: 1 or SEQ ID NO: 3, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789–6792.

Conservative Mutations

In addition variants of the sHIF sequence that may exist in the population, the skilled artisan will further appreciate that changes can be introduced by mutation into the nucleotide sequence of SEQ ID NO: 1 or SEQ ID NO: 3, thereby leading to changes in the amino acid sequence of the encoded sHIF protein, without altering the functional ability of the sHIF protein. For example, nucleotide substitutions leading to amino acid substitutions at "non-essential" amino acid residues can be made in the sequence of SEQ ID NO: 1 or SEQ ID NO: 3. A "non-essential" amino acid residue is a residue that can be altered from the wild-type sequence of sHIF without altering the biological activity, whereas an "essential" amino acid residue is required for biological activity. For example, amino acid residues that are conserved among the sHIF proteins of the present invention, are predicted to be particularly unamenable to alteration.

Another aspect of the invention pertains to nucleic acid molecules encoding sHIF proteins that contain changes in amino acid residues that are not essential for activity. Such sHIF proteins differ in amino acid sequence from SEQ ID NO:2 or SEQ ID NO:4, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:2 or SEQ ID NO:4. Preferably, the protein encoded by the nucleic acid is at least about 80% homologous to SEQ ID NO:2 or SEQ ID NO:4, more preferably at least about 90%, 95%, 98%, and most preferably at least about 99% homologous to SEQ ID NO:2 or SEQ ID NO:4.

An isolated nucleic acid molecule encoding a sHIF protein homologous to the protein of SEQ ID NO:2 or SEQ ID NO:4 can be created by introducing one or more nucleotide substitutions, additions or deletions into the nucleotide sequence of SEQ ID NO:1 such that one or more amino acid substitutions, additions or deletions are introduced into the encoded protein.

Mutations can be introduced into the nucleotide sequence of SEQ ID NO: 1 or SEQ ID NO: 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in sHIF is replaced with another amino acid residue from the same side chain family. Alternatively, in another embodiment, mutations can be introduced randomly along all or part of a sHIF coding sequence, such as by saturation mutagenesis, and the resultant mutants can be screened for sHIF biological activity to identify mutants that retain activity. Following mutagenesis of SEQ ID NO: 1 or SEQ ID NO: 3 the encoded protein can be expressed by any recombinant technology known in the art and the activity of the protein can be determined.

sHIF Recombinant Expression Vectors and Host Cells

Another aspect of the invention pertains to vectors, preferably expression vectors, containing a nucleic acid encoding a sHIF protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., sHIF proteins, mutant forms of sHIF proteins, fusion proteins, etc.).

The recombinant expression vectors of the invention can be designed for expression of sHIF proteins in prokaryotic or eukaryotic cells. For example, sHIF proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOL- OGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the sHIF expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, sHIF can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banedji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to sHIF mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, sHIF protein can be expressed in bacterial cells such as *E. coli*, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding sHIF or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) sHIF protein. Accordingly, the invention further provides methods for producing sHIF protein using the host cells of the invention. In one embodiment, the method comprises culturing the host cell of invention (into which a recombinant expression vector encoding sHIF protein has been introduced) in a suitable medium such that sHIF protein is produced. In another embodiment, the method further comprises isolating sHIF protein from the medium or the host cell.

Transgenic sHIF Animals

The host cells of the invention can also be used to produce non-human transgenic animals. For example, in one embodiment, a host cell of the invention is a fertilized oocyte or an embryonic stem cell into which sHIF protein-coding sequences have been introduced. Such host cells can then be used to create non-human transgenic animals in which exogenous sHIF sequences have been introduced into their genome or homologous recombinant animals in which endogenous sHIF sequences have been altered. Such animals are useful for studying the function and/or activity of sHIF protein and for identifying and/or evaluating modulators of sHIF protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous sHIF gene has been altered by homologous recombination between the endogenous gene and an exogenous DNA molecule introduced into a cell of the animal, e.g., an embryonic cell of the animal, prior to development of the animal.

A transgenic animal of the invention can be created by introducing sHIF-encoding nucleic acid into the male pronuclei of a fertilized oocyte (e.g., by microinjection, retroviral infection) and allowing the oocyte to develop in a pseudopregnant female foster animal. Sequences including SEQ ID NO: 1 or SEQ ID NO: 3 can be introduced as a transgene into the genome of a non-human animal. Alternatively, a non-human homologue of the human sHIF gene, such as a mouse sHIF gene, can be isolated based on hybridization to the human sHIF cDNA (described further supra) and used as a transgene. Intronic sequences and polyadenylation signals can also be included in the transgene to increase the efficiency of expression of the transgene. A tissue-specific regulatory sequence(s) can be operably-linked to the sHIF transgene to direct expression of sHIF protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the sHIF transgene in its genome and/or expression of sHIF mRNA in tissues or cells of the animals. A transgenic founder animal can then be used to breed additional animals carrying the transgene. Moreover, transgenic animals carrying a transgene-encoding sHIF protein can further be bred to other transgenic animals carrying other transgenes.

To create a homologous recombinant animal, a vector is prepared which contains at least a portion of a sHIF gene into which a deletion, addition or substitution has been introduced to thereby alter, e.g., functionally disrupt, the sHIF gene. The sHIF gene can be a human gene (e.g., the DNA of SEQ ID NO: 1 or SEQ ID NO: 3), but more preferably, is a non-human homologue of a human sHIF gene. For example, a mouse homologue of human sHIF gene of SEQ ID NO: 1 or SEQ ID NO: 3 can be used to construct a homologous recombination vector suitable for altering an endogenous sHIF gene in the mouse genome. In one embodiment, the vector is designed such that, upon homologous recombination, the endogenous sHIF gene is functionally disrupted (i.e., no longer encodes a functional protein; also referred to as a "knock out" vector).

Alternatively, the vector can be designed such that, upon homologous recombination, the endogenous sHIF gene is mutated or otherwise altered but still encodes functional protein (e.g., the upstream regulatory region can be altered to thereby alter the expression of the endogenous sHIF protein). In the homologous recombination vector, the altered portion of the sHIF gene is flanked at its 5'- and 3'-termini by additional nucleic acid of the sHIF gene to allow for homologous recombination to occur between the exogenous sHIF gene carried by the vector and an endogenous sHIF gene in an embryonic stem cell. The additional flanking sHIF nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced sHIF gene has homologously-recombined with the endogenous sHIF gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

sHIF Antibodies

Also included in the invention are antibodies to sHIF proteins, or fragments of sHIF proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$, and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated sHIF-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2 or SEQ ID NO:4, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of sHIF-related protein that is located on the surface of the protein, e.g., a hydrophilic region. A hydrophobicity analysis of the human sHIF-related protein sequence will indicate which regions of a sHIF-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.* 133:3001 (1984); Brodeur et al., *Monoclonal Antibody Production Techniques and Applications*, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 *Immunol Today* 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 EMBO J., 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')₂ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')₂ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')₂ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc?R), such as Fc?R1 (CD64), Fc?R11 (CD32) and Fc?RIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (sHIF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene tri-aminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Method of Modulating Expression of a Hypoxia Inducible Gene

Also provides by the invention is a method of increasing the expression of at least one hypoxia inducible gene, i.e., a gene that is activated by a hypoxia inducible factor. The method includes contacting the cell with an expression vector containing a polynucleotide encoding a sHIF of the invention under conditions that allow expression of the nucleic acid sequence contained in the vector thereby providing for increased expression of hypoxia inducible genes in the cell. Such genes include, for example, those encoding VEGF, glucose transporters, glycolytic enzymes, IGF-2, IGF binding proteins and the like.

The cell can be any cell capable of expressing the hypoxia inducible gene.

The cell population that is exposed to, i.e., contacted with, the expression vector can be any number of cells, i.e., one or more cells, and can be provided in vitro, in vivo, or ex vivo.

Method of Treating Hypoxia or Ischemia Related Tissue Damage and Modulating Angiogenesis or Vascularization The invention also provides various methods of treating, i.e., reducing, preventing or delaying the onset of HIF-1 mediated disorders, modulating angiogenesis or vascularization. Examples of HIF-1 mediated disorders include hypoxia or ischemia related tissue damage. The subject is preferably a mammal. The mammal can be, e.g., a human, non-human primate, mouse, rat, dog, cat, horse, or cow. In various aspects the subject include patients with coronary, cerebral, or peripheral arterial disease and patients with one or more non-healing wounds.

According to the method of the invention, substantially purified sHIF-1alpha mutein or the polynucleotide sequence encoding sHIF-1alpha in an appropriate vector is introduced into a subject for the treatment or prevention of hypoxia/ischemia-related tissue damage or to modulated angiogenesis or vascularization.

The relevant clinical conditions treated by the methods and compositions of the invention include ischemia due to disease of the cerebral, coronary, or peripheral circulation. One therapeutic goal is to promote angiogenesis in the isehemic tissue by overexpression of sHIF-, which would dimerize with endogenous HIF-1beta, bind to specific DNA sequences, and activate transcription of hypoxia-inducible genes relevant to angiogenesis, such as, but not limited to, the gene encoding vascular endothelial growth factor (VEGF), a known HIF-1 target gene (J. A. Forsythe et al., Mol Cell Biol 16:4604, 1996; N. V. Iyer et al., Genes Dev 12: 149, 1998). The rationale for using HIF-1alpha is that because it is a transcription factor that controls the expression of multiple genes involved in angiogenesis it will give a superior clinical outcome compared to treatment with a single angiogenic factor such as VEGF. However, the method of delivery of DNA to the tissue site is in no way affected by the identity of the particular gene being delivered. Further, many patients with coronary artery disease do not have reduced myocardial blood flow or hypoxia at rest. It is only when they are active and require increased myocardial blood flow that they experience anginal symptoms resulting from myocardial ischemia. Alternatively, a narrowed coronary vessel may become completely occluded either by spasm or a clot, resulting in a myocardial infarction (heart attack). Therefore the goal of the treatment with the stable form of HIF-1alpha is to induce angiogenesis in these patients, even if there is no hypoxia at the time, in order to prevent heart attacks. Accordingly, the sHIF compositions of the invention provide prophylactic as well as therapeutic treatment regimens.

The present invention provides the introduction of polynucleotides encoding sHIF-1alpha for the treatment of hypoxia-related disorders, which are improved or ameliorated by expression of the HIF-1alpha polypeptide. Such therapy would achieve its therapeutic effect by introduction of the sHIF-1alpha polynucleotide into cells exposed to hypoxic conditions. HIF-1alpha is thus expressed in both the hypoxic and surrounding nonhypoxic tissues, such that it can dimerize with HIF-1beta (which is present in excess in hypoxic and nonhypoxic cells), and activate the transcription of downstream target genes. Examples of genes which can be activated by HIF-1 are vascular endothelial growth factor, glucose transporters, glycolytic enzymes, and insulin-like growth factor 2. These genes mediate important adaptive responses to hypoxia including angiogenesis and glycolysis, and prevention of cell death.

The herein-described sHIF polypetide and nucleic acids when used therapeutically are referred to herein as "Therapeutics". Methods of administration of Therapeutics include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. Various delivery systems are known and can be used to administer a Therapeutic of the present invention including, e.g.: (i) encapsulation in liposomes, microparticles, microcapsules; (ii) recombinant cells capable of expressing the Therapeutic; (iii) receptor-mediated endocytosis (See, e.g., Wu and Wu, 1987. *J Biol Chem* 262: 4429–4432); (iv) construction of a Therapeutic nucleic acid as part of a retroviral, adenoviral or other vector, and the like. In one embodiment of the present invention, the Therapeutic may be delivered in a vesicle, in particular a liposome. In a liposome, the protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,837,028; and U.S. Pat. No. 4,737,323, all of which are incorporated herein by reference. In yet another embodiment, the Therapeutic can be delivered in a controlled release system including, e.g.: a delivery pump (See, e.g., Saudek, et al., 1989. *New Engl J Med* 321:574 and a semi-permeable polymeric material (See, e.g., Howard, et al., 1989. *J Neurosurg* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. *Proc Natl Acad Sci USA* 88:1864–1868), and the like. Alternatively, a nucleic acid Therapeutic can be introduced intracellularly and incorporated within host cell DNA for expression, by homologous recombination or remain episomal.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. However, suitable dosage ranges for intravenous administration of the Therapeutics of the present invention are generally about 20–500 micrograms (µg) of active compound per kilogram (Kg) body weight. Suitable dosage ranges for intranasal administration are generally about 0.01 μg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient The duration of intravenous therapy using the Therapeutic of the present invention will vary, depending on the severity of the disease being treated and the condition and potential idiosyncratic response of each individual patient. Ultimately the attending physician will decide on the appropriate duration of intravenous therapy using the pharmaceutical composition of the present invention.

Cells may also be cultured ex vivo in the presence of therapeutic agents or proteins of the present invention in order to proliferate or to produce a desired effect on or activity in such cells. Treated cells can then be introduced in vivo for therapeutic purposes.

Gene Therapy

In one aspect of the invention a nucleic acid or nucleic acids encoding a sHIF polypeptide, or functional derivatives thereof, are administered by way of gene therapy. Gene therapy refers to therapy that is performed by the administration of a specific nucleic acid to a subject. In this aspect of the invention, the nucleic acid produces its encoded peptide(s), which then serve to exert a therapeutic effect by modulating function of an aforementioned disease or disorder. e.g., ischemia or hypoxia. Any of the methodologies relating to gene therapy available within the art may be used in the practice of the present invention. See e.g., Goldspiel, et al., 1993. *Clin Pharm* 12: 488–505.

In a preferred embodiment, the therapeutic comprises a nucleic acid that is part of an expression vector expressing any one or more of the aforementioned sHIF polypeptides, or fragments, derivatives or analogs thereof, within a suitable host. In a specific embodiment, such a nucleic acid possesses a promoter that is operably-linked to coding region(s) of a sHIF polypeptide. The promoter may be inducible or constitutive, and, optionally, tissue-specific. The promoter may be, e.g., viral or mammalin in origin. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. *Proc Natl Acad Sci USA* 86: 8932–8935. In yet another embodiment the nucleic acid that is delivered remains episomal and induces an endogenous and otherwise silent gene.

Delivery of the therapeutic nucleic acid into a patient may be either direct (i.e., the patient is directly exposed to the nucleic acid or nucleic acid-containing vector) or indirect (i.e., cells are first contacted with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429–4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599–618. The chosen technique should provide for the stable transfer of the nucleic acid to the cell, such that the nucleic acid is expressible by the cell. Preferably, said transferred nucleic acid is heritable and expressible by the cell progeny. In an alterantive embodiment, the transferred nucleic acid remains episomal and induces the expression of the otherwise silent endogenous nucleic acid.

In preferred embodiments of the present invention, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells) or liver cells. The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973–985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

Pharmaceutical Compositions

The compounds, e.g., sHIF polypeptides, nucleic acid endoding sHIF polypetides, and sHIF antibodies (also referred to herein as "active compounds") of the invention, and derivatives, fragments, analogs and homologs thereof, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifingal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a sHIF polypeptide or sHIF encoding nucleic acid) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

The invention will be further described in the following examples, which do not limit the scope of the invention described in the claims.

EXAMPLES

Example 1

Figure 1B:
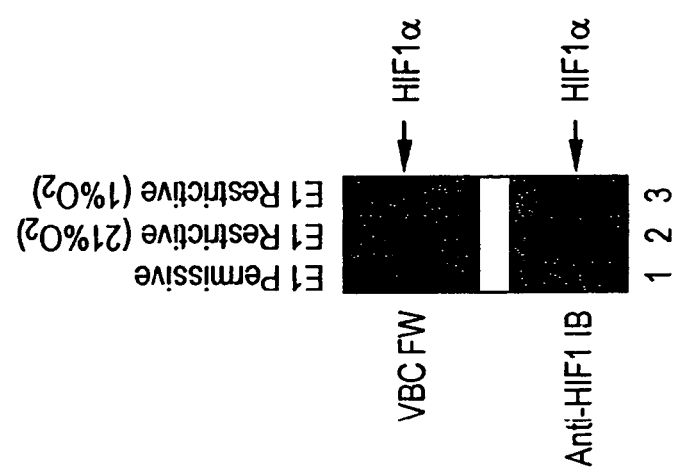
FIG. 1B. is a photograph of a blot showing that pVHL binds to a modified form of HIF. VBC farwestern and anti-HIF1α immunoblot analysis of ts20 cells grown at the restrictive temperature under hypoxic or normoxic conditions.
Figure 1A:
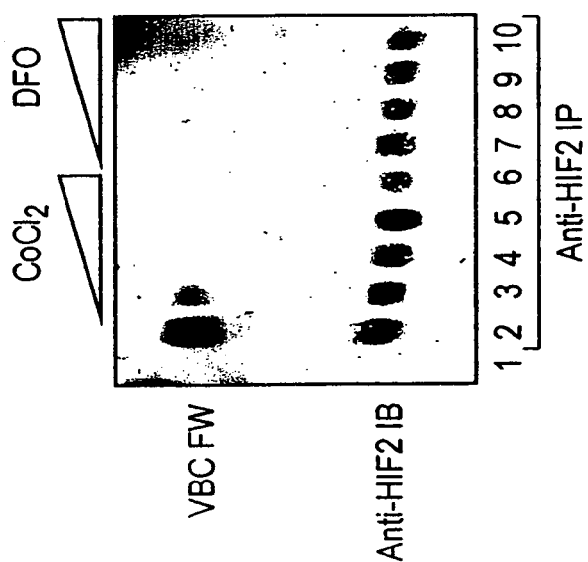
FIG. 1A. is a photograph of a blot showing that pVHL binds to a modified form of HIF. pVHL-defective renal carcinoma cells were treated with increasing amounts of desferrioxamine (2, 10, 100, 1000 µm) or cobalt chloride (2, 10, 100, 1000 µm) and immunoprecipitated with control (lane 1) or anti-HIF2α antibody. Bound proteins were detected by anti-HIF2α immunoblot (IB) or by farwestern (FW) analysis with purified pVHL/elongin B/elongin C (VBC) complexes.

Effect of Cobalt Chloride and Desferoxamine Treatment on pVHL-HIF Interations pVHL-defective renal carcinoma cells were treated with increasing amounts of cobalt chloride or desferoxamine. The untreated cells contained high levels of HIF2α, which bound directly to recombinant pVHL/elongin B/elongin C (VBC) in far western blot assays (FIG. 1A). In contrast, VBC did not recognize HIF2α isolated from cells treated with cobalt chloride or desferoxamine.

Hypoxia, in contrast to cobalt chloride and desferoxamine, inhibits HIF polyubiquitination but not the physical association of pVHL and HIF. Suggesting that physiological regulation of HIF by hypoxia is mechanistically distinct from the pharmacological effects of cobalt chloride and desferoxamine. Exposure of cell extracts to oxygen, however, might have allowed for reformation of pVHL/HIF complexes postlysis. To address this, mouse cells (ts20) with a temperature-sensitive mutation in the E1 ubiquitin-activating enzyme (19) were grown at the non-permissive temperature under either hypoxic or normoxic conditions so that HIF would accumulate in the presence or absence of oxygen (20). The cells were then rapidly lysed and farwestern blotted with VBC. VBC only recognized the HIF that accumulated in the presence of oxygen (FIG. 1B). Comparable induction of HIF1α in these two settings was confirmed by anti-HIF1α immunblot analysis. Collectively, these experiments indicate that the interaction of pVHL with HIF is governed by a posttranslational modification of HIF which is oxygen and iron dependent.

Figure 1D:
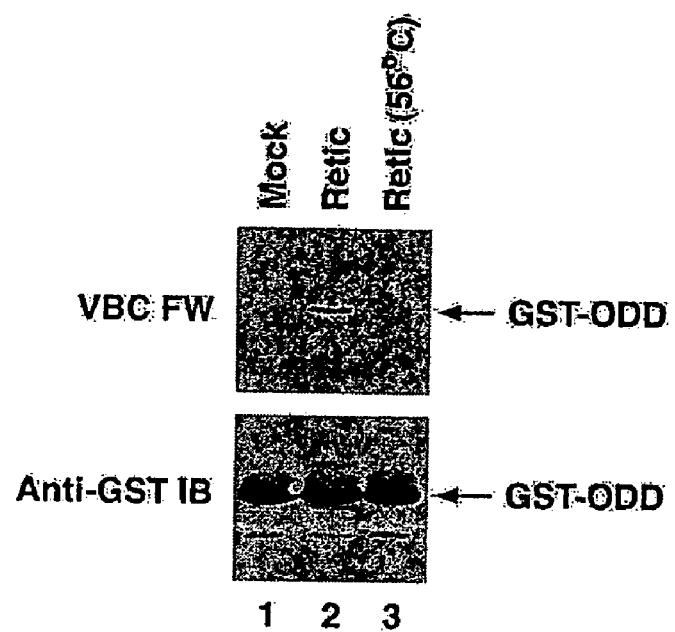
FIG. 1D. is a photograph of a blot showing that pVHL binds to a modified form of HIF. GST-HIF1α(530–652), containing the oxygen-dependent degradation domain (ODD), was produced in *E. Coli*, recovered on glutathione sepharose, and incubated with rabbit reticulocyte lysate for 90 min at 30° C. After stringent washes the GST-ODD protein was subjected to VBC farwestern and anti-GST immunoblot analysis. In lane 3 the reticulocyte lysate was first heat inactivated for 20 min. After stringent washes the GST-ODD protein was subjected to VBC farwestern and anti-GST immunoblot analysis.

Example 2 pVHL Recognizes a Specifically Modified Form of HIF pVHL binds to a region of HIF1α called the oxygen-dependent degradation domain (ODD)(7). It was observed that pVHL bound to HIF produced in rabbit reticulocyte lysate but not to HIF produced in wheat germ extracts or in *E. coli* (16). Furthermore, wheat germ or *E. coli*-derived HIF acquired pVHL binding activity after preincubation with human, rabbit, or *Xenopus* cell extracts at 37° C. (16). For example, glutathione S-transferase-ODD fusion proteins produced in *E. coli* were not recognized by VBC unless preincubated with a rabbit reticulocyte lysate (FIG. 1C). VBC did not recognize GST-ODD fusion proteins incubated with a heat-inactivated reticulocyte lysate (FIG. 1D). These results indicate that pVHL recognizes a modified form of HIF and that this modification is carried out by a factor present in a variety of vertebrate cell extracts.

Example 3

Analysis of the Modified HIF Recognized by PVHL

Figure 2A:
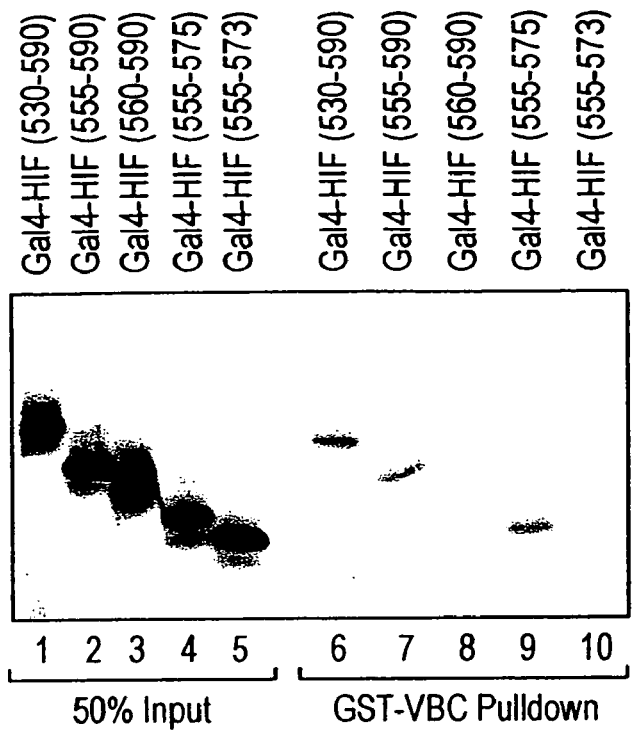
FIG. 2A. is a photograph of a blot showing binding of the indicated $^{35}$S-labeled Gal4-HIF1α fusion proteins to immobilized GST-pVHL, elongin B, elongin C complexes.
Figure 2B:
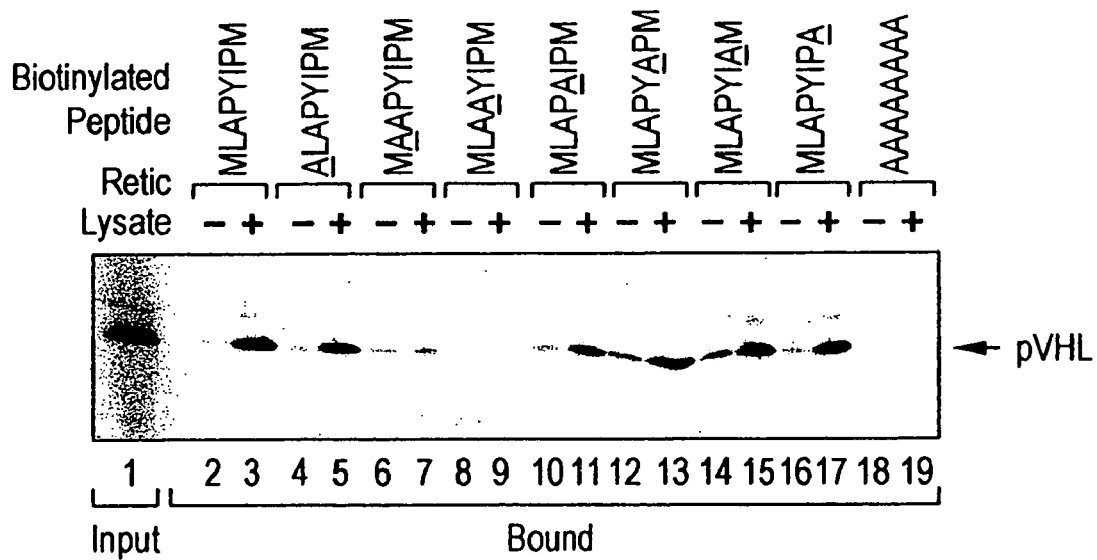
FIG. 2B. is a photograph of a blot showing binding of $^{35}$S-labeled pVHL to biotinylated HIF1α(556–575) peptides with the indicated substitutions of residues 561–568. '+' indicates preincubation of peptide with unprogrammed reticulocyte lysate prior to addition of pVHL.
Figure 2C:
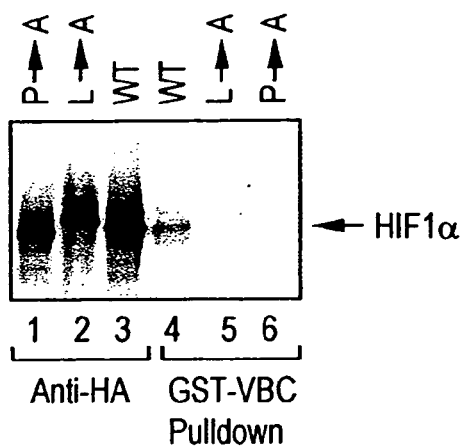
FIG. 2C is a photograph of a blot showing $^{35}$S-labeled wild-type (WT), Pro564Ala, and Leu562Ala full-length HA-HIF1α
Figure 2D:
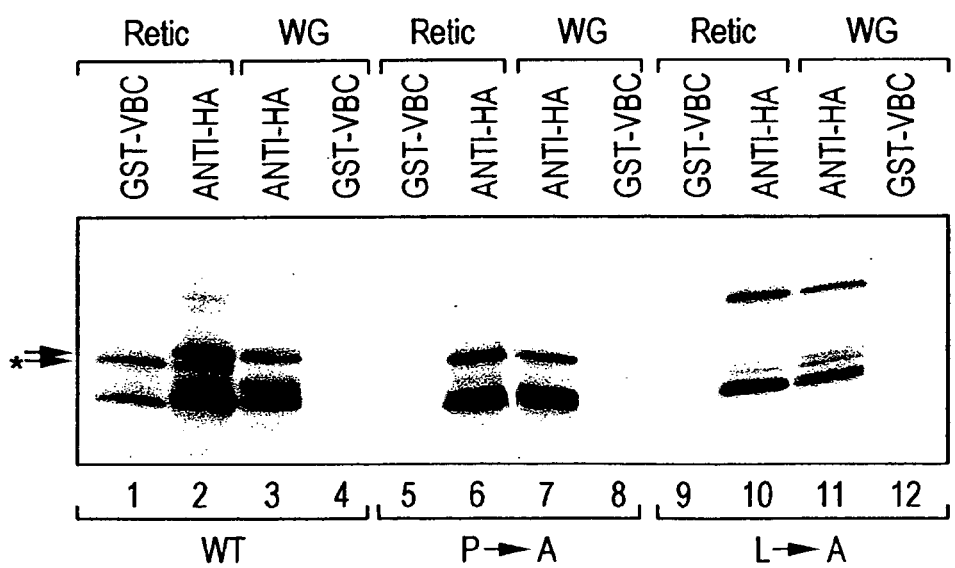
FIG. 2D s a photograph of a blot showing $^{35}$S-labeledGal4-HA-HIF1α(530–652). Proteins were immunoprecipitated with anti-HA antibody or captured with immobilized GST-VBC complexes. WG=wheat germ extract; Retic=rabbit reticulocyte lysate.

To determine the nature of this modification, we determined the region of HIF that binds to pVHL. Gal4-HIF fusion proteins containing HIF residues 555–575 bound specifically to immobilized GST-VHL, elongin B, elongin C complexes (FIGS. 2A and 2E) (13, 17). Likewise, a biotinylated peptide corresponding to HIF residues 556–575 bound to pVHL following preincubation with reticulocyte lysate (FIG. 2B) (18). As noted by others, this region of HIF contains a highly conserved 8-mer (MLAPYIPM) (SEQ ID NO: 8) (FIG. 2E) which, when mutated to 8 consecutive alanines, leads to HIF stabilization (19). An alanine scan of this region showed that Leu562 and Pro564 were essential for specific binding to pVHL (FIG. 2B). In contrast, mutation of the one potential phosphoacceptor in this peptide, Tyr565, did not affect pVHL binding, consistent with an earlier study in which a Tyr565Phe mutation did not affect HIF stability (20). Moreover, phosphatase treatment did not affect the binding of pVHL to GST-ODD in these assays (16).

Importantly, mutation of either Leu562 or Pro564 in the context of full-length HIF1α or a Gal4-ODD fusion protein abrogated pVHL binding activity (FIG. 2, C and D). It was noted that Gal4-ODD synthesized in reticulocyte lysate contained an electrophoretically distinct band that was absent from wheat germ-derived Gal4-ODD preparations (FIG. 2D). The corresponding protein bound to VBC and was undetectable among the Leu562Ala and Pro564Ala translation products, suggesting that it might contain a posttranslational modification of Leu562 or Pro564. 2-D protein gel electrophoresis suggested that this putative modification did not involve a change in protein charge (16).

Figure 3A:
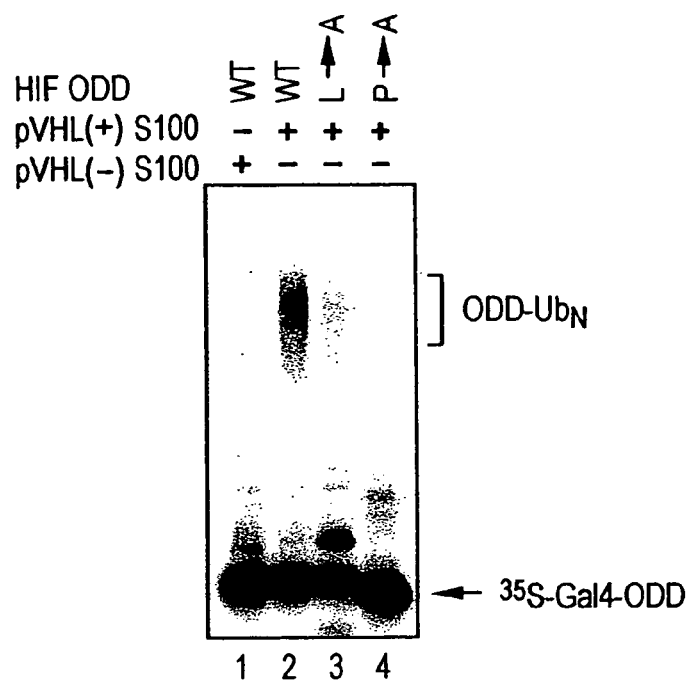
FIG. 3A is a photograph of a blot showing in vitro ubiquitination of $^{35}$S-labeled wild-type, Leu562Ala, and Pro564Ala Gal4-HA-HIF1α(530–652) in the presence of S100 extracts prepared from pVHL-defective renal carcinoma cells stably transfected with a vector producing wild-type pVHL or with empty vector.
Figure 3B:
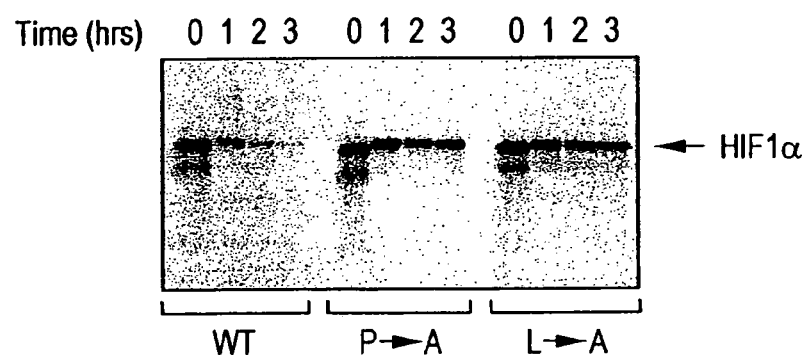
FIG. 3B is a photograph of a blot showing in vitro degradation of $^{35}$S-labeled wild-type, Leu562Ala, and Pro564Ala in *Xenopus* egg extracts.

Consistent with the pVHL-binding assays, Gal4-HIF fusion proteins with the Leu562Ala or Pro564Ala mutations displayed diminished pVHL-dependent polyubiquitination in vitro (FIG. 3A) (13). Qualitatively similar results were obtained with the corresponding full-length HIF1α species (16). Likewise, full-length HIF1α Pro564Ala and HIF1α Leu562Ala were more stable than wild-type HIF1α in degradation assays performed with *Xenopus* extracts (21) (FIG. 3B).

Example 4

Determination that HIF Modification is a Proline Hydroxylation

Figure 4B:
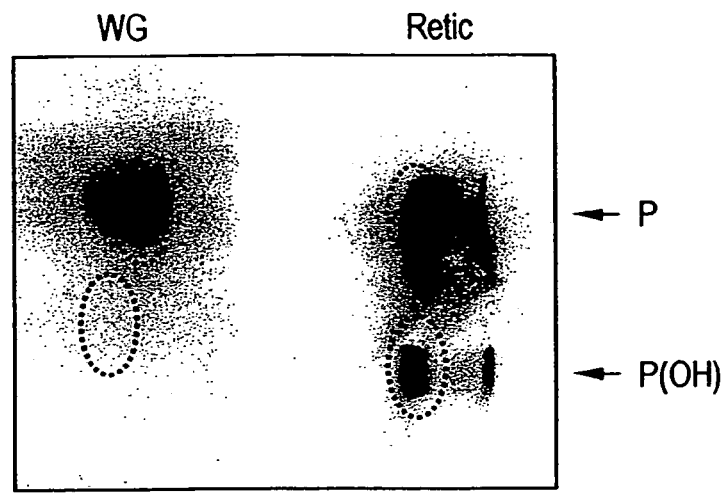
FIG. 4B is a photograph showing Gal4-HA-HIF (555–575) translated in vitro in the presence of $^3$H-Proline with rabbit reticulocyte lysate or wheat germ extract, hydrolyzed, and analyzed by TLC. Dashed circles indicate positions of ninhydrin stained proline and hydroxyproline markers.

To determined whether the HIF modification was proline hydroxylation biotinylated HIF (556–575) peptides were incubated with rabbit reticulocyte lysate, eluted the peptides with free biotin, and analyzed them by mass spectrometry (23). In these experiments Met561 and Met568 were replaced with alanine to prevent spurious oxidation of the methionines. These substitutions did not affect pVHL binding (16). The HIF peptide samples that had been pretreated with rabbit reticulocyte lysate contained a second peak in MALDI-TOF analysis that corresponded to an increase in molecular weight of 16 (FIG. 4A). This peak was not detectable in peptide preparations prior to incubation with reticulocyte lysate nor in reticulocyte-treated Leu562Ala and Pro564Ala peptides (FIG. 4A)(16). Electrospray ion trap tandem mass spectrometry (MS/MS) confirmed the addition of +16 at Pro 564 and excluded such a modification of Leu 562 (24). Moreover, ion trap MS/MS of the reticulocyte-treated HIF (556–575) peptide produced a product ion spectrum that was identical to that obtained with a synthetic HIF (556–575) peptide containing hydroxyproline at position 564 (16). Gal4-HIF(555–575) in was translated in the presence of 3H-Proline using rabbit reticulocyte lysate or wheat germ extract, isolated it using an electrophoretic gel, and subjected it to acid hydrolysis and thin layer chromatography (17, 25). The Gal4-HIF produced in rabbit reticulocyte lysate, but not in wheat germ, contained hydroxyproline (FIG. 4B).

Figure 5A:
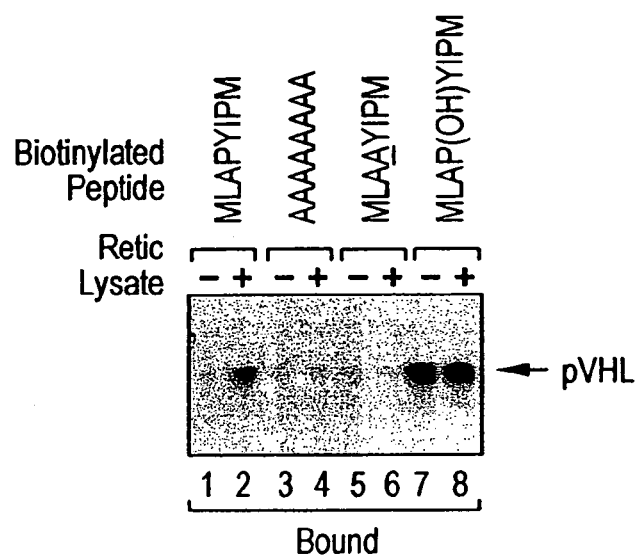
FIG. 5A is a photograph of a blot showing binding of $^{35}$S-labeled pVHL to biotinylated HIF1α(556–575) peptides with the indicated substitutions of residues 561–568.
Figure 5B:
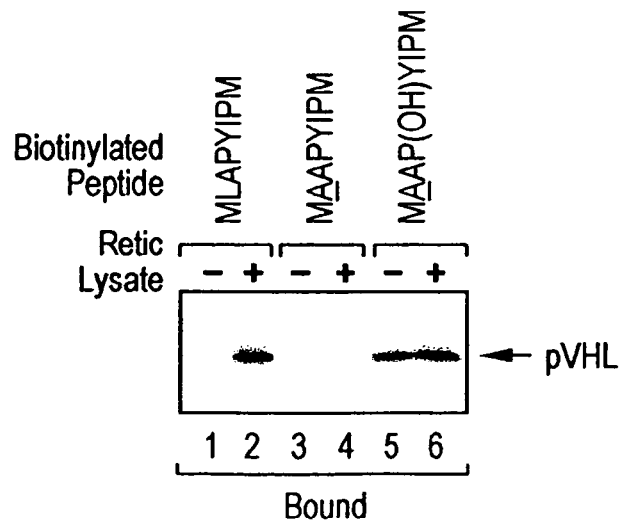
FIG. 5B is a photograph of a blot showing binding of $^{35}$S-labeled pVHL to biotinylated HIF1α(556–575) peptides with the indicated substitutions of residues 561–568.

As expected, the HIF (556–575) peptide containing hydroxyproline at position 564 bound to pVHL with or without pretreatment with reticulocyte lysate (FIG. 5A). The mass spectrometry analysis of the Leu562Ala peptide showed that Leu562 was required for HIF modification (FIG. 4A) but left open the possibility that it was not required for binding to pVHL. Indeed, pVHL bound to a HIF (556–575) peptide with the Leu562Ala substitution and hydroxyproline at residue 564 (FIG. 5B). This suggests that Leu562 facilitates hydroxylation of Pro 564.

Example 5

Analysis of Hyydroxylated HIF Interacts with Cell-Derived pVHL Complexes

Figure 3C:
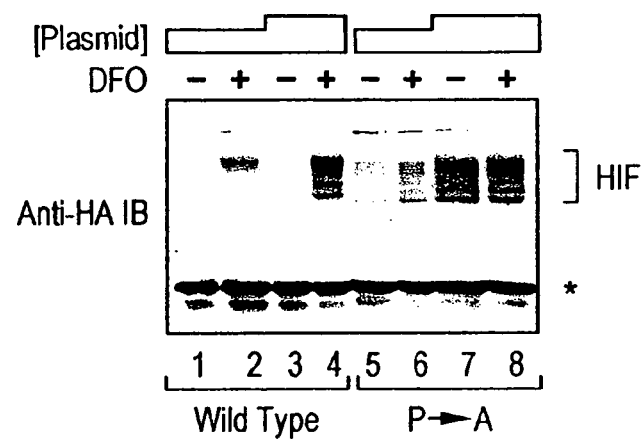
FIG. 3C is a photograph of a blot showing anti-HA immunoblot analysis of COS7 cells transiently transfected with 1.5 (lanes 1, 2, 5, 6) or 3.5 µg (lanes 3, 4, 7, 8) of plasmids encoding wild-type or Pro564Ala HA-HIF1α and then transferred to media that did or did not contain desferrioxamine.
Figure 5C:
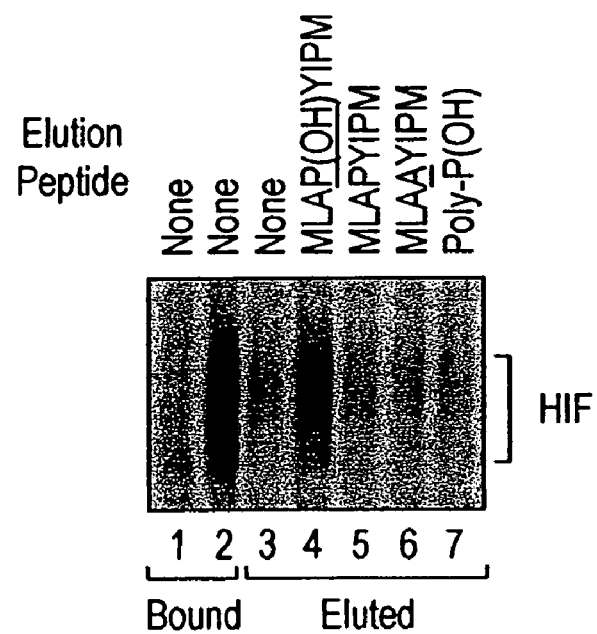
FIG. 5C is a photograph of a blot showing ts20 cells stably transfected to produce HA-pVHL were metabolically labeled at restrictive (lane 1) or permissive (lanes 2–6) temperature and immunoprecipitated anti-HIF1α (lane 1 and 2) or anti-HA antibody (lanes 3–7). Bound proteins were eluted by boiling in sample buffer (lane 1 and 2) or treatment with the indicated peptides, resolved by polyacrylamide gel electrophoresis, and detected by autoradiography.
Figure 5D:
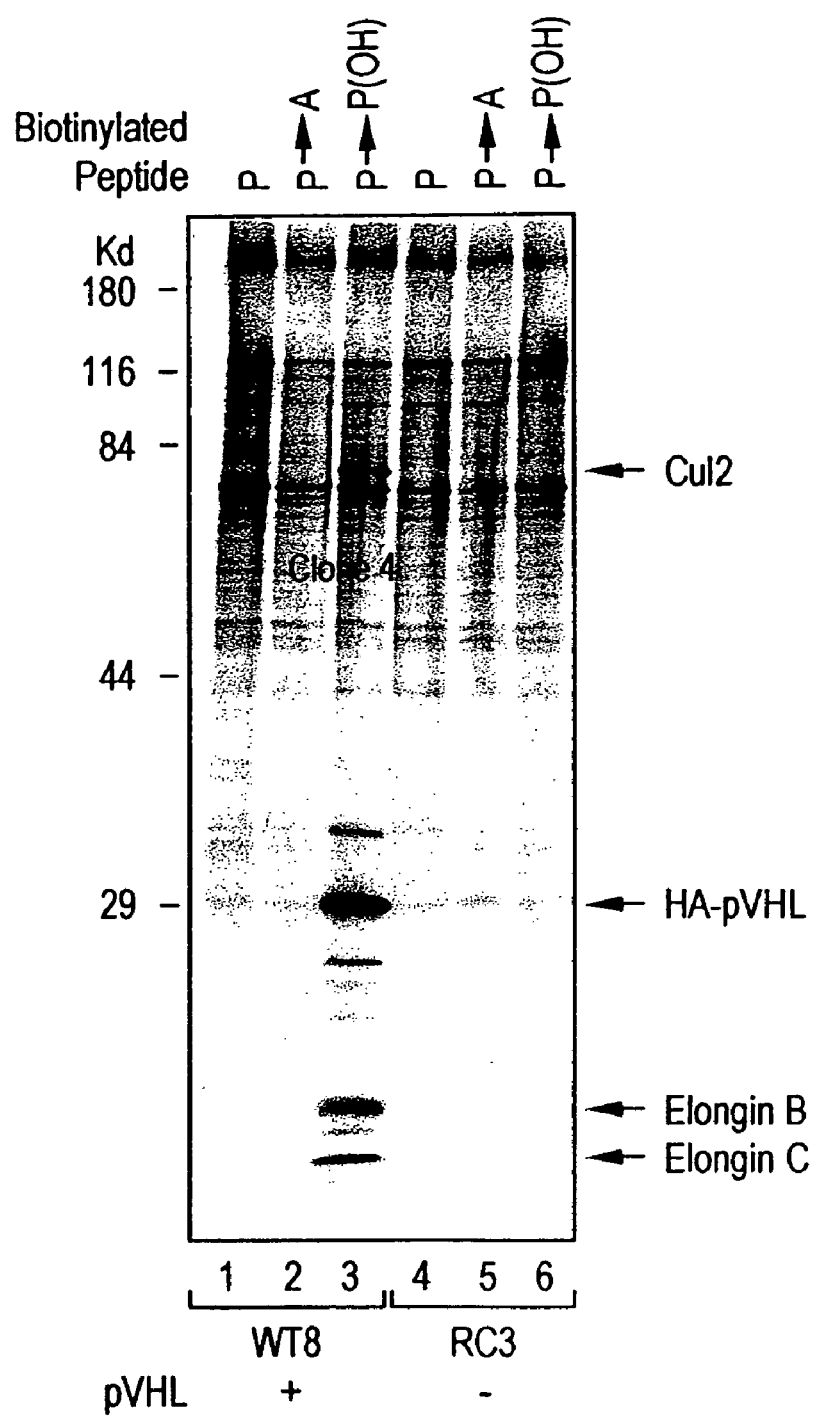
FIG. 5D is a photograph of a blot showing pVHL-defective renal carcinoma cells that had been stably transfected with a vector producing wild-type pVHL (WT8) or with empty vector (RC3) were metabolically labeled with $^{35}$S methionine, lysed, and incubated with immobilized biotinylated HIF1α(556–575) peptides with the indicated substitutions of residue 564. Specifically bound proteins were detected by autoradiography.

Ts20 cells were engineered to produce HA-tagged pVHL (26). It was found that HIF bound to HA-pVHL at the restrictive temperature could be eluted by the hydroxylated HIF (556–575) peptide but not the unmodified peptide (27) (FIG. 5C). Moreover, HIF was not eluted by the HIF (556–575) Pro564Ala peptide or by a poly-hydroxyproline peptide (FIG. 5C). Affinity chromatography was carried out with immobolized peptides and metabolically labeled matched renal carcinoma cells that do (WT8) or do not (RC3) produce HA-pVHL (18, 27, 28). The hydroxylated HIF (556–575) peptide specifically bound to pVHL as well as to proteins with the expected electrophoretic mobilities of the pVHL-associated proteins elongin B, elongin C, and Cul2 (FIG. 5D). These results indicate that pVHL recognizes a proline hydroxylated epitope present in HIF1α. Consistent with this idea, a HIF 1α mutant containing a Pro564Ala mutation showed enhanced stability in COS7 cells and was insensitive to the hypoxia-mimetic desferrioxamine (FIG. 3C).

Example 6

Production of a HIF 1 Alpha Pro564Ala Mutant

The HIF1alpha Pro564Ala mutant cDNA was generated by two-step PCR. A wild-type HIF1alpha cDNA was PCR amplified with Primer A (GCGCGGATCCGCCACCATGGAG) (SEQ ID NO: 9)/Primer B (CATTGGGATATAAGCAGCTAACATCTC) (SEQ ID NO: 10) or Primer C (GAGATGTTAGCTGCTTATATCCCAATG) (SEQ ID NO: 11)/Primer D (GCGCCAATTGTCAGTTAACTTG) (SEQ ID NO: 12). The PCR products were then mixed and amplified with Primer A and D. The resulting PCR product was digested with Bam HI and Mun I and ligated to pcDNA3.0-HA digested with Bam HI and Eco RI. The resulting cDNA was authenticated by DNA sequencing.

Example 7

Production of a HIF 2 Alpha Pro531Ala Mutant

The HIF2 alpha Pro531 Ala mutant cDNA was generated by two-step PCR. A wild-type HIF2alpha cDNA was PCR amplified with Primer A (GCGCGGATCCGCCACCATGACA) (SEQ ID NO: 13)/Primer B (CATGGGGATATAAGCTGCCAGTGTCTC) (SEQ ID NO: 14) or Primer C (GAGACACTGGCAGCTTATATCCCCATG) (SEQ ID NO: 15)/Primer D (GCGCCAATTGTCAGGTGGCCTGGTC) (SEQ ID NO: 16). The PCR products were then mixed and amplified with Primer A and D. The resulting PCR product was digested with Bam HI and Mun I and ligated with pcDNA3.0-HA vector digested with Bam HI and Eco RI. The resulting cDNA was authenticated by DNA sequencing.

Example 8

HIF Mutein Polypeptide Sequence

A HIF mutein polypeptide sequence is shown in SEQ ID NO:5 The mutation is shown in bold-font. A leucine at position 562 in wild type HIF alpha is replaced with an alanine in SEQ ID NO:.5.

```
  1 megaggandk kkisserrke ksrdaarsrr skesevfyel ahqlplphnv sshldkasvm   (SEQ ID NO:5)

61 rltisylrvr klldagdldi eddmkaqmnc fylkaldgfv mvltddgdmi yisdnvnkym 121 gltqfeltgh svfdfthpcd heemremlth rnglvkkgke qntqrsfflr mkctltsrgr 181 tmniksatwk vlhctghihv ydtnsnqpqc gykkppmtcl vlicepiphp snieipldsk 241 tflsrhsldm kfsycderit elmgyepeel lgrsiyeyyh aldsdhltkt hhdmftkgqv
```

-continued

```
301 ttgqyrmlak rggyvwvetq atviyntkns qpqcivcvny vvsgiiqhdl ifslqqtecv 361 lkpvessdmk mtqlftkves edtsslfdkl kkepdaltll apaagdtiis ldfgsndtet 421 ddqqleevpl yndvmlpspn eklqninlam splptaetpk plrssadpal nqevalklep 481 npeslelsft mpqiqdqtps psdgstrqss pepnspseyc fyvdsdmvne fklelveklf 541 aedteaknpf stqdtdldle maapyipmdd dfqlrsfdql splesssasp esaspqstvt 601 vfqqtqiqep tanattttat tdelktvtkd rmedikilia spspthihke ttsatsspyr 661 dtqsrtaspn ragkgvieqt ekshprspnv lsvalsqrtt vpeeelnpki lalqnaqrkr 721 kmehdgslfq avgigtllqq pddhaattsl swkrvkgcks seqngmeqkt iilipsdlac 781 rllgqsmdes glpqltsydc evnapiqgsr nllqgeellr aldqvn
```

Example 9

HIF Mutein Polypeptide Sequence

A HIF mutein polypeptide sequence is shown in SEQ ID NO:6 The mutation is shown in bold-font. A leucine at position 562 and a proline at position 564 in wild type HIF alpha are replaced with alanines in SEQ ID NO:.6.

Example 10

HIF Mutein Polypeptide Sequence

A HIF mutein polypeptide sequence is shown in SEQ ID NO:7 The mutation is shown in bold-font. A proline at position 402, a leucine at position 562, and a proline at position 564 in wild type HIF alpha are replaced with alanines in SEQ ID NO:.7.

```
  1 megaggandk kkisserrke ksrdaarsrr skesevfyel ahqlplphnv sshldkasvm 61 rltisylrvr klldagdldi eddmkaqmnc fylkaldgfv mvltddgdmi yisdnvnkym 121 gltqfeltgh svfdfthpcd heemremlth rnglvkkgke qntqrsfflr mkctltsrgr 181 tmniksatwk vlhctghihv ydtnsnqpqc gykkppmtcl vlicepiphp snieipldsk 241 tflsrhsldm kfsycderit elmgyepeel lgrsiyeyyh aldsdhltkt hhdmftkgqv 301 ttgqyrmlak rggyvwvetq atviyntkns qpqcivcvny vvsgiiqhdl ifslqqtecv 361 lkpvessdmk mtqlftkves edtsslfdkl kkepdaltll apaagdtiis ldfgsndtet 421 ddqqleevpl yndvmlpspn eklqninlam splptaetpk plrssadpal nqevalklep 481 npeslelsft mpqiqdqtps psdgstrqss pepnspseyc fyvdsdmvne fklelveklf 541 aedteaknpf stqdtdldle maaayipmdd dfqlrsfdql splesssasp esaspqstvt 601 vfqqtqiqep tanattttat tdelktvtkd rmedikilia spspthihke ttsatsspyr 661 dtqsrtaspn ragkgvieqt ekshprspnv lsvalsqrtt vpeeelnpki lalqnaqrkr 721 kmehdgslfq avgigtllqq pddhaattsl swkrvkgcks seqngmeqkt iilipsdlac 781 rllgqsmdes glpqltsydc evnapiqgsr nllqgeellr aldqvn
```

```
  1 megaggandk kkisserrke ksrdaarsrr skesevfyel ahqlplphnv sshldkasvm   (SEQ ID NO:7)
 61 rltisylrvr klldagdldi eddmkaqmnc fylkaldgfv mvltddgdmi yisdnvnkym
121 gltqfeltgh svfdfthpcd heemremlth rnglvkkgke qntqrsfflr mkctltsrgr
181 tmniksatwk vlhctghihv ydtnsnqpqc gykkppmtcl vlicepiphp snieipldsk
241 tflsrhsldm kfsycderit elmgyepeel lgrsiyeyyh aldsdhltkt hhdmftkgqv
301 ttgqyrmlak rggyvwvetq atviyntkns qpqcivcvny vvsgiiqhdl ifslqqtecv
361 lkpvessdmk mtqlftkves edtsslfdkl kkepdaltll aaaagdtiis ldfgsndtet
421 ddqqleevpl yndvmlpspn eklqninlam splptaetpk plrssadpal nqevalklep
481 npeslelsft mpqiqdqtps psdgstrqss pepnspseyc fyvdsdmvne fklelveklf
541 aedteaknpf stqdtdldle maaayipmdd dfqlrsfdql splesssasp esaspqstvt
601 vfqqtqiqep tanatttat  tdelktvtkd rmedikilia spspthihke ttsatsspyr
661 dtqsrtaspn ragkgvieqt ekshprspnv lsvalsqrtt vpeeelnpki lalqnaqrkr
721 kmehdgslfq avgigtllqq pddhaattsl swkrvkgcks seqngmeqkt iilipsdlac
781 rllgqsmdes glpqltsydc evnapiqgsr nllggeellr aldqvn
```

REFERENCES AND NOTES

1. G. Semenza, *Annu. Rev. Cell Dev. Biol.* 15, 551 (1999).
2. R. Wenger, *J Exp. Biol.* 203, 1253 (2000).
3. G. Semenza, *Cell* 98, 281 (1999).
4. H. Zhu, F. Bunn, *Resp. Phys.* 115, 239 (1999).
5. M. Ivan, W. G. Kaelin, *Curr. Opin. Gen. and Dev.* 11, 27 (2001).
6. C. E. Stebbins, W. G. Kaelin, N. P. Pavletich, *Science* 284, 455 (1999).
7. M. Ohh, et al., *Nature Cell Biol.* 2, 423 (2000).
8. T. Kamura, et al., *Proc. Natl. Acad. Sci.* (*USA*) 97, 10430 (2000).
9. M. Cockman, et al., *J. Biol. Chem.* 275, 25733 (2000).
10. K. Tanimoto, Y. Makino, T. Pereira, L. Poellinger, *EMBO J.* 19, 4298 (2000).
11. R. Deshaies, *Annu. Rev. Cell. Dev. Biol.* 15, 435 (1999).
12. P. Maxwell, et al., *Nature* 399, 271 (1999).
13. Farwestern blot assays, GST-pulldown assays, and in vitro ubiquitination assays were performed as described in (7).
14. D. Chowdary, J. Dermody, K. Jha, H. Ozer, *Mol. Cell. Biol.* 14, 1997 (1994).
15. Normoxic cells were grown at restrictive (39° C.) or permissive temperature (33° C.) for 12 hours. Hypoxic cells were grown in the presence of 1% $O_2$ for 6 hours at permissive temperature and then at the restrictive temperature for 12 hours. The cells were lysed by incubation in EBC [50 mM tris-HCl (pH 8.0), 120 mM NaCl, 0.5% NP-40] for 5 min at 4° C. Following centrifugation at 14,000 g for 3 min, the clarified lysate was boiled in SDS.
16. M. Ivan, M. Ohh, J. Asara, W. S. Lane, and W. G. Kaelin (Unpublished Data)
17. Coupled in vitro transcription/translation of $^{35}$S-labeled proteins was performed according to the manufacturer's instructions (TNT, Promega, Madison, Wis.). In vitro translation of $^3$H-P-labeled Gal4-HIF (555–575) was done similarly in a 2 ml reaction containing 450 PI L-[2,3,4,5–3H]-proline (New England Nuclear).
18. For peptide binding studies, 1 μg of biotinylated peptide was bound to 30 μl of monomeric avidin agarose (Pierce). Where indicated, the peptide was preincubated with 50 μl of rabbit reticulocyte lysate for 90 min at 30° C. The agarose was then washed 3 times with NETN [20 mM tris-HCl (pH 8.0), 100 mM NaCl, 1 mM EDTA, 0.5% N—P40) and used in binding reactions containing 4 μl $_{35}$S-HA-pVHL in 500 μl of EBC or 500 μl $^{35}$S-radiolabeled cell extract (equivalent to cells from a sub-confluent 100 mm dish). After a 1 hour incubation at 4° C. the agarose was washed 4 times with NETN. Bound proteins were eluted by boiling in SDS-containing sample buffer and detected by autoradiography.
19. V. Srinivas, L. Zhang, X. Zhu, J. Caro, *Biochem. Biophys. Res. Commun.* 260, 557 (1999).
20. C. Pugh, J. O'Rourke, M. Nagao, J. Gleadle, P. Ratcliffe, *J. Biol. Chem.* 272, 11205 (1997).
21. *Xenopus* egg extracts were prepared [A. Salic, E. Lee, L. Mayer, M. Kirschner, *Mol. Cell.* 5, 523 (2000)] and stored frozen. Degradation reactions contained 8 μl of egg extract, 0.1 μl of 100 mg/ml cyclohexamide, 0.25 μl of energy regeneration mix, 0.25 μl of bovine ubiquitin, and 0.4 μl of $^{35}$S-radiolabeled HIF and were carried out at room temperature. At the indicated timepoints 1 μl aliquots were removed and placed in sample buffer. Samples were resolved on 5–15% gradient gels and analyzed by autoradiography.
22. K. I. Kivirikko, J. Myllyhaiju, *Matrix Biol.* 16, 357 (1998).
23. HPLC-purified peptide (1 μg) was bound to 30 μl monomeric avidin agarose and incubated with 100 μl of rabbit reticulocyte lysate at room temperature for 1 hour with tumbling. After a brief centrifugation, the reticulocyte lysate was removed, fresh reticulocyte lysate was added, and the cycle was repeated 6 times. The agarose was then washed 4 times with NETN and once with PBS. The modified peptide was eluted in 50 μl of 20 mM ammonium acetate [pH 7.0], 2 mM biotin. Proline 564 hydroxylation was confirmed by MS/MS using microcapillary HPLC directly coupled to a Finnigan LCQ DECA quadrupole ion trap mass spectrometer equipped with a custom nanoelectrospray source. Targeted ion MS/MS (TIMM) of the doubly protonated ion at m/z 1267 for the HIF (556–575) peptides was performed with an isolation width of 2.5 dalton and relative collision energy of 30%.
24. www. science on-line address
25. 2 ml of $_3$H-P-labeled Gal4-HIF (555–575) in vitro translate was immunoprecipitated with 50 µg of anti-HA antibody (12CA5, Roche), resolved on a 12% SDS-polyacrylamide gel, and transferred to a Polyvinylidene Fluoride (PVDF) membrane. Gal4-HIF (555–575) was visualized by autoradiography and the corresponding region of the membrane was excised and hydrolyzed by incubation in 100 µl of 10 N HCl at 105° C. for 3 hours. Samples were evaporated to dryness, resuspended in 20 µl H$_2$O containing 10 µg of unlabeled proline and 4-OH proline (Sigma), and resolved by 2-D thin layer chromatography using phenol-distilled H$_2$O in the first dimension and N-butanol-acetic acid-H$_2$O in the second dimension [J. Ludlow, R. Consigli, *J Virol* 1989 63, 2881–4 (1989)]. Following visualization of standards with ninhydrin, radiolabeled proline was detected by autoradiography.
26. ts20 cells were transfected with pIRES-HA-VHL, pIRES-HA-VHL (Y98H), or pIRES-Neo (Invitrogen) and selected in the presence of 1 mg/ml G418. Individual G418-resistant colonies were isolated using cloning cylinders and expanded. Cells producing HA-VHL or HA-VHL (Y98H) were identified by anti-HA immunoblot analysis.
27. ts20 cells were grown at the restrictive or permissive temperature for 14 hours, methionine-starved for 90 min, and then grown in the methionine-free media supplemented with $^{35}$S-met (500 µCi/ml) for 90 min. Cells were washed once with cold PBS, lysed in EBC, and immunoprecipitated with anti-HA (12CA5; Roche) or anti-HIF1α (NB100–105; Novus). After 5 washes with NETN, bound proteins were eluted by boiling in sample buffer or by incubation in 65 µl of PBS containing 7 µg of the indicated peptide. 786O subclones were starved for 1 hour, grown in the methionine-free media supplemented with $^{35}$S-met (500 µpCi/ml) for 3 hours, washed once with ice cold PBS, and lysed in EBC.
28. O. Iliopoulos, A. Kibel, S. Gray, W. G. Kaelin, *Nature Med.* 1, 822 (1995).
29. P. Jaakkola, et al., *Science* (In Press).
30. Y. Takahashi, S. Takahashi, Y. Shiga, T. Yoshimi, T. Miura, *J. Biol. Chem.* 275, 14139 (2000).
31. C. Levene, C. Bates, *Biochim. Biophys. Acta* 444, 446 (1976).
32. M. Bickel, et al., *Hepatology* 28, 404 (1998).
33. T. Franklin, W. Morris, P. Edwards, M. Large, R. Stephenson, *Biochem J* 353, 333 (2001).
34. L. Friedman, et al., *Proc. Natl. Acad. Sci. USA* 97, 4736 (2000).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid encoding a hypoxia inducible factor α (HIFα) mutein polypeptide, wherein said HIFα mutein polypeptide comprises the amino acid sequence set forth in SEQ ID NO: 2 except wherein: A) the amino acid residue at position 402 of said polypeptide sequence is not proline; B) the amino acid residue at position 562 of said polypeptide sequence is not leucine; and C) the amino acid residue at position 564 of said polypeptide sequence is any amino acid other than proline.

2. An expression vector comprising a nucleic acid of claim 1 operably linked to a promoter.

3. An host cell containing the expression vector of claim 2.

4. A composition comprising the nucleic acid of claim 1 and a pharmaceutically acceptable carrier.

5. The isolated nucleic acid of claim 1, wherein the polypeptide sequence is SEQ ID NO: 7.

6. An isolated nucleic acid encoding a hypoxia inducible factor α (HIF α) mutein, wherein said HIF α mutein polypeptide comprises the amino acid sequence set forth in SEQ ID NO:4.

* * * * *

SEQUENCE LISTING

```
<160> NUMBER OF SEQ ID NOS: 35

<210> SEQ ID NO 1
<211> LENGTH: 2481
<212> TYPE: DNA
<213> ORGANISM: Artificial Sequence
<220> FEATURE:
<223> OTHER INFORMATION: Description of Artificial Sequence: Encodes HIF
      Mutein

<400> SEQUENCE: 1
atggagggcg ccggcggcgc gaacgacaag aaaaagataa gttctgaacg tcgaaaagaa      60
aagtctcgag atgcagccag atctcggcga agtaaagaat ctgaagtttt ttatgagctt     120
gctcatcagt tgccacttcc acataatgtg agttcgcatc ttgataaggc ctctgtgatg     180
aggcttacca tcagctattt gcgtgtgagg aaacttctgg atgctggtga tttggatatt     240
gaagatgaca tgaaagcaca gatgaattgc ttttatttga aagccttgga tggttttgtt     300
atggttctca cagatgatgg tgacatgatt tacatttctg ataatgtgaa caaatacatg     360
ggattaactc agtttgaact aactggacac agtgtgtttg attttactca tccatgtgac     420
catgaggaaa tgagagaaat gcttacacac agaaatggcc ttgtgaaaaa gggtaaagaa     480
caaaacacac agcgaagctt ttttctcaga atgaagtgta ccctaactag ccgaggaaga     540
actatgaaca taaagtctgc aacatggaag gtattgcact gcacaggcca cattcacgta     600
tatgatacca acagtaacca acctcagtgt gggtataaga aaccacctat gacctgcttg     660
gtgctgattt gtgaacccat tcctcaccca tcaaatattg aaattccttt agatagcaag     720
actttcctca gtcgacacag cctggatatg aaattttctt attgtgatga agaattacc      780
```

```
gaattgatgg gatatgagcc agaagaactt ttaggccgct caatttatga atattatcat    840
gctttggact ctgatcatct gaccaaaact catcatgata tgtttactaa aggacaagtc    900
accacaggac agtacaggat gcttgccaaa agaggtggaa atgtctgggt tgaaactcaa    960
gcaactgtca tatataacac caagaattct caaccacagt gcattgtatg tgtgaattac   1020
gttgtgagtg gtattattca gcacgacttg attttctccc ttcaacaaac agaatgtgtc   1080
cttaaaccgg ttgaatcttc agatatgaaa atgactcagc tattcaccaa agttgaatca   1140
gaagatacaa gtagcctctt tgacaaactt aagaaggaac ctgatgcttt aactttgctg   1200
gccccagccg ctggagacac aatcatatct ttagattttg gcagcaacga cacagaaact   1260
gatgaccagc aacttgagga agtaccatta tataatgatg taatgctccc ctcacccaac   1320
gaaaaattac agaatataaa tttggcaatg tctccattac ccaccgctga aacgccaaag   1380
ccacttcgaa gtagtgctga ccctgcactc aatcaagaag ttgcattaaa attagaacca   1440
aatccagagt cactggaact ttcttttacc atgcccagat tcaggatcag acacctagt   1500
ccttccgatg gaagcactag acaaagttca cctgagccta atagtcccag tgaatattgt   1560
ttttatgtgg atagtgatat ggtcaatgaa ttcaagttgg aattggtaga aaactttttt   1620
gctgaagaca cagaagcaaa gaacccattt tctactcagg acacagattt agacttggag   1680
atgttagctg cttatatccc aatggatgat gacttccagt acgttccttc gatcagttg   1740
tcaccattag aaagcagttc cgcaagccct gaaagcgcaa gtcctcaaag cacagttaca   1800
gtattccagc agactcaaat acaagaacct actgctaatg ccaccactac cactgccacc   1860
actgatgaat taaaaacagt gacaaaagac cgtatggaag acattaaaat attgattgca   1920
tctccatctc ctacccacat acataaagaa actactagtg ccacatcatc accatataga   1980
gatactcaaa gtcggacagc ctcaccaaac agagcaggaa aaggagtcat gaacagaca   2040
gaaaaatctc atccaagaag ccctaacgtg ttatctgtcg ctttgagtca agaactaca   2100
gttcctgagg aagaactaaa tccaaagata ctagctttgc agaatgctca gagaaagcga   2160
aaaatggaac atgatggttc acttttttcaa gcagtaggaa ttggaacatt attacagcag   2220
ccagacgatc atgcagctac tacatcactt tcttggaaac gtgtaaaagg atgcaaatct   2280
agtgaacaga tggaatgga gcaaaagaca attattttaa tacccttga tttagcatgt   2340
agactgctgg ggcaatcaat ggatgaaagt ggattaccac agctgaccag ttatgattgt   2400
gaagttaatg ctcctataca aggcagcaga aacctactgc agggtgaaga attactcaga   2460
gctttggatc aagttaactg a                                            2481
```

<210> SEQ ID NO 2
<211> LENGTH: 826
<212> TYPE: PRT
<213> ORGANISM: Artificial Sequence
<220> FEATURE:
<223> OTHER INFORMATION: Description of Artificial Sequence: HIF Mutein

<400> SEQUENCE: 2

Met Glu Gly Ala Gly Gly Ala Asn Asp Lys Lys Lys Ile Ser Ser Glu
 1               5                  10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile

-continued

```
                50                  55                  60
Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
                115                 120                 125

Gly His Ser Val Phe Asp Phe Thr His Pro Cys Asp His Glu Glu Met
130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
                180                 185                 190

His Cys Thr Gly His Ile His Val Tyr Asp Thr Asn Ser Asn Gln Pro
                195                 200                 205

Gln Cys Gly Tyr Lys Lys Pro Pro Met Thr Cys Leu Val Leu Ile Cys
                210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
                275                 280                 285

Lys Thr His His Asp Met Phe Thr Lys Gly Gln Val Thr Thr Gly Gln
                290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
                355                 360                 365

Met Lys Met Thr Gln Leu Phe Thr Lys Val Glu Ser Glu Asp Thr Ser
                370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
                435                 440                 445

Ala Met Ser Pro Leu Pro Thr Ala Glu Thr Pro Lys Pro Leu Arg Ser
                450                 455                 460

Ser Ala Asp Pro Ala Leu Asn Gln Glu Val Ala Leu Lys Leu Glu Pro
465                 470                 475                 480
```

Asn Pro Glu Ser Leu Glu Leu Ser Phe Thr Met Pro Gln Ile Gln Asp
            485                 490                 495

Gln Thr Pro Ser Pro Ser Asp Gly Ser Thr Arg Gln Ser Ser Pro Glu
        500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Ala Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 3
<211> LENGTH: 2613
<212> TYPE: DNA
<213> ORGANISM: Artificial Sequence
<220> FEATURE:
<223> OTHER INFORMATION: Description of Artificial Sequence: Encodes HIF
      Mutein

<400> SEQUENCE: 3
atgacagctg acaaggagaa gaaaaggagt agctcggaga ggaggaagga gaagtcccgg     60

```
gatgctgcgc ggtgccggcg gagcaaggag acggaggtgt tctatgagct ggcccatgag      120
ctgcctctgc cccacagtgt gagctcccat ctggacaagg cctccatcat gcgactggca      180
atcagcttcc tgcgaacaca caagctcctc tcctcagttt gctctgaaaa cgagtccgaa      240
gccgaagctg accagcagat ggacaacttg tacctgaaag ccttggaggg tttcattgcc      300
gtggtgaccc aagatggcga catgatcttt ctgtcagaaa acatcagcaa gttcatggga      360
cttacacagg tggagctaac aggacatagt atctttgact tcactcatcc ctgcgaccat      420
gaggagattc gtgagaacct gagtctcaaa atggctctg gttttgggaa aaaaagcaaa       480
gacatgtcca cagagcggga cttcttcatg aggatgaagt gcacggtcac caacagaggc      540
cgtactgtca acctcaagtc agccacctgg aaggtcttgc actgcacggg ccaggtgaaa      600
gtctacaaca actgccctcc tcacaatagt ctgtgtggct acaaggagcc cctgctgtcc      660
tgcctcatca tcatgtgtga accaatccag cacccatccc acatggacat ccccctggat      720
agcaagacct tcctgagccg ccacagcatg gacatgaagt tcacctactg tgatgacaga      780
atcacagaac tgattggtta ccaccctgag gagctgcttg gccgctcagc ctatgaattc      840
taccatgcgc tagactccga gaacatgacc aagagtcacc agaacttgtg caccaagggt      900
caggtagtaa gtggccagta ccggatgctc gcaaagcatg ggggctacgt gtggctggag      960
acccagggga cggtcatcta caaccctcgc aacctgcagc ccagtgcat catgtgtgtc       1020 aactacgtcc tgagtgagat tgagaagaat gacgtggtgt tctccatgga ccagactgaa      1080
tccctgttca gccccacct gatggccatg aacagcatct ttgatagcag tgcaaggggg       1140
gctgtgtctg agaagagtaa cttcctattc accaagctaa aggaggagcc cgaggagctg      1200
gcccagctgg ctcccacccc aggagacgcc atcatctctc tggatttcgg gaatcagaac      1260
ttcgaggagt cctcagccta tgcaaggcc atcctgcccc cgagccagcc atgggccacg       1320
gagttgagga gccacagcac ccagagcgag gctgggagcc tgcctgcctt caccgtgccc      1380
caggcagctg ccccgggcag caccacccc agtgccacca gcagcagcag cagctgctcc       1440
acgcccaata gccctgaaga ctattacaca tcttttggata cgacctgaa gattgaagtg      1500 attgagaagc tcttcgccat ggacacagag gccaaggacc aatgcagtac ccagacggat      1560
ttcaatgagc tggacttgga gacactggca gcttatatcc ccatggacgg ggaaggcttc      1620
cagctaagcc ccatctgccc cgaggagcgg ctcttggcgg agaacccaca gtccaccccc      1680
cagcactgct tcagtgccat gacaaacatc ttccagccac tggcccctgt agccccgcac      1740
agtcccttcc tcctggacaa gtttcagcag cagctggaga gcaagaagac agagcccgag      1800
cgccggccca tgtcctccat cttctttgat gccggaagca agcatccct gccaccgtgc       1860 tgtggccagg ccagcacccc tctctcttcc atgggggca gatccaacac ccagtggccc       1920
ccagatccac cattcatttt tgggcccaca aagtgggccg tcggggatca gcgcacagag      1980
ttcttgggag cagcgccgtt ggggccccct gtctctccac ccatgtctc caccttcaaa       2040 acaaggtctg caaagggttt tggggctcga ggcccaaacg tgctgagtcc ggccatggta      2100
gccctctcca acaagctgaa gctgaagcga cagctggagt atgaaaagca agccttccag      2160
gacccgagcg gggggaccc acctggtggc agcacctcac atttgatgtg aaacgatg        2220 aagaacctca ggggtgggag ctgccctttg atgccggaca agccactgag cgcaaatgta      2280
cccaatgata agctcaccca aaactccatg aggggcctgg gccatcccct gagacatctg      2340
ccgctgccac agcctccatc tgccatcagt cccggggaga acagcaagag caggttcccc      2400
```

```
ccacagtgct acgccaccca gtaccaggac tacagcctgt cgtcagccca caaggtgtca    2460
ggcatggcaa gccggctgct cgggccctca tttgagtcct acctgctgcc cgaactgacc    2520
agatatgacc gtgaggtgaa agtgcccgtg ctgggaagct ccacgctcct gcaaggaggg    2580
gacctcctca gagccctgga ccaggccacc tga                                 2613
```

```
<210> SEQ ID NO 4
<211> LENGTH: 870
<212> TYPE: PRT
<213> ORGANISM: Artificial Sequence
<220> FEATURE:
<223> OTHER INFORMATION: Description of Artificial Sequence: HIF Mutein

<400> SEQUENCE: 4
```

| | | | | | | | | | | | | | | |
|---|---|---|---|---|---|---|---|---|---|---|---|---|---|---|
| Met | Thr | Ala | Asp | Lys | Glu | Lys | Lys | Arg | Ser | Ser | Ser | Glu | Arg | Arg |
| 1 | | | | 5 | | | | | 10 | | | | | 15 |
| Lys | Glu | Lys | Ser | Arg | Asp | Ala | Ala | Arg | Cys | Arg | Arg | Ser | Lys | Glu |
| | | | | 20 | | | | | 25 | | | | | 30 |
| Thr | Glu | Val | Phe | Tyr | Glu | Leu | Ala | His | Glu | Leu | Pro | Leu | Pro | His |
| | | | | 35 | | | | | 40 | | | | | 45 |
| Ser | Val | Ser | Ser | His | Leu | Asp | Lys | Ala | Ser | Ile | Met | Arg | Leu | Ala |
| | | | | 50 | | | | | 55 | | | | | 60 |
| Ile | Ser | Phe | Leu | Arg | Thr | His | Lys | Leu | Leu | Ser | Ser | Val | Cys | Ser |
| 65 | | | | | 70 | | | | | 75 | | | | | 80 |
| Glu | Asn | Glu | Ser | Glu | Ala | Glu | Ala | Asp | Gln | Gln | Met | Asp | Asn | Leu |
| | | | | 85 | | | | | 90 | | | | | 95 |
| Tyr | Leu | Lys | Ala | Leu | Glu | Gly | Phe | Ile | Ala | Val | Val | Thr | Gln | Asp |
| | | | | 100 | | | | | 105 | | | | | 110 |
| Gly | Asp | Met | Ile | Phe | Leu | Ser | Glu | Asn | Ile | Ser | Lys | Phe | Met | Gly |
| | | | | 115 | | | | | 120 | | | | | 125 |
| Leu | Thr | Gln | Val | Glu | Leu | Thr | Gly | His | Ser | Ile | Phe | Asp | Phe | Thr |
| | | | | 130 | | | | | 135 | | | | | 140 |
| His | Pro | Cys | Asp | His | Glu | Glu | Ile | Arg | Glu | Asn | Leu | Ser | Leu | Lys |
| 145 | | | | | 150 | | | | | 155 | | | | | 160 |
| Asn | Gly | Ser | Gly | Phe | Gly | Lys | Lys | Ser | Lys | Asp | Met | Ser | Thr | Glu |
| | | | | 165 | | | | | 170 | | | | | 175 |
| Arg | Asp | Phe | Phe | Met | Arg | Met | Lys | Cys | Thr | Val | Thr | Asn | Arg | Gly |
| | | | | 180 | | | | | 185 | | | | | 190 |
| Arg | Thr | Val | Asn | Leu | Lys | Ser | Ala | Thr | Trp | Lys | Val | Leu | His | Cys |
| | | | | 195 | | | | | 200 | | | | | 205 |
| Thr | Gly | Gln | Val | Lys | Val | Tyr | Asn | Asn | Cys | Pro | Pro | His | Asn | Ser |
| | | | | 210 | | | | | 215 | | | | | 220 |
| Leu | Cys | Gly | Tyr | Lys | Glu | Pro | Leu | Leu | Ser | Cys | Leu | Ile | Ile | Met |
| 225 | | | | | 230 | | | | | 235 | | | | | 240 |
| Cys | Glu | Pro | Ile | Gln | His | Pro | Ser | His | Met | Asp | Ile | Pro | Leu | Asp |
| | | | | 245 | | | | | 250 | | | | | 255 |
| Ser | Lys | Thr | Phe | Leu | Ser | Arg | His | Ser | Met | Asp | Met | Lys | Phe | Thr |
| | | | | 260 | | | | | 265 | | | | | 270 |
| Tyr | Cys | Asp | Asp | Arg | Ile | Thr | Glu | Leu | Ile | Gly | Tyr | His | Pro | Glu |
| | | | | 275 | | | | | 280 | | | | | 285 |
| Glu | Leu | Leu | Gly | Arg | Ser | Ala | Tyr | Glu | Phe | Tyr | His | Ala | Leu | Asp |
| | | | | 290 | | | | | 295 | | | | | 300 |
| Ser | Glu | Asn | Met | Thr | Lys | Ser | His | Gln | Asn | Leu | Cys | Thr | Lys | Gly |
| 305 | | | | | 310 | | | | | 315 | | | | | 320 |
| Gln | Val | Val | Ser | Gly | Gln | Tyr | Arg | Met | Leu | Ala | Lys | His | Gly | Gly |
| | | | | | | | | | | | | | | |

Tyr Val Trp Leu Glu Thr Gln Gly Thr Val Ile Tyr Asn Pro Arg Asn Leu Gln Pro Gln Cys

-continued

```
            325                 330                 335
Ile Met Cys Val Asn Tyr Val Leu Ser Glu Ile Glu Lys Asn Asp Val
            340                 345                 350
Val Phe Ser Met Asp Gln Thr Glu Ser Leu Phe Lys Pro His Leu Met
            355                 360                 365
Ala Met Asn Ser Ile Phe Asp Ser Ser Gly Lys Gly Ala Val Ser Glu
            370                 375                 380
Lys Ser Asn Phe Leu Phe Thr Lys Leu Lys Glu Glu Pro Glu Glu Leu
385                             390                 395                 400
Ala Gln Leu Ala Pro Thr Pro Gly Asp Ala Ile Ile Ser Leu Asp Phe
                    405                 410                 415
Gly Asn Gln Asn Phe Glu Glu Ser Ser Ala Tyr Gly Lys Ala Ile Leu
                    420                 425                 430
Pro Pro Ser Gln Pro Trp Ala Thr Glu Leu Arg Ser His Ser Thr Gln
                    435                 440                 445
Ser Glu Ala Gly Ser Leu Pro Ala Phe Thr Val Pro Gln Ala Ala Ala
            450                 455                 460
Pro Gly Ser Thr Thr Pro Ser Ala Thr Ser Ser Ser Ser Cys Ser
465                 470                 475                 480
Thr Pro Asn Ser Pro Glu Asp Tyr Tyr Thr Ser Leu Asp Asn Asp Leu
                    485                 490                 495
Lys Ile Glu Val Ile Glu Lys Leu Phe Ala Met Asp Thr Glu Ala Lys
                    500                 505                 510
Asp Gln Cys Ser Thr Gln Thr Asp Phe Asn Glu Leu Asp Leu Glu Thr
            515                 520                 525
Leu Ala Ala Tyr Ile Pro Met Asp Gly Glu Gly Phe Gln Leu Ser Pro
            530                 535                 540
Ile Cys Pro Glu Glu Arg Leu Leu Ala Glu Asn Pro Gln Ser Thr Pro
545                 550                 555                 560
Gln His Cys Phe Ser Ala Met Thr Asn Ile Phe Gln Pro Leu Ala Pro
                    565                 570                 575
Val Ala Pro His Ser Pro Phe Leu Leu Asp Lys Phe Gln Gln Gln Leu
            580                 585                 590
Glu Ser Lys Lys Thr Glu Pro Glu Arg Arg Pro Met Ser Ser Ile Phe
            595                 600                 605
Phe Asp Ala Gly Ser Lys Ala Ser Leu Pro Pro Cys Cys Gly Gln Ala
            610                 615                 620
Ser Thr Pro Leu Ser Ser Met Gly Gly Arg Ser Asn Thr Gln Trp Pro
625                 630                 635                 640
Pro Asp Pro Pro Leu His Phe Gly Pro Thr Lys Trp Ala Val Gly Asp
                    645                 650                 655
Gln Arg Thr Glu Phe Leu Gly Ala Ala Pro Leu Gly Pro Pro Val Ser
                    660                 665                 670
Pro Pro His Val Ser Thr Phe Lys Thr Arg Ser Ala Lys Gly Phe Gly
                    675                 680                 685
Ala Arg Gly Pro Asn Val Leu Ser Pro Ala Met Val Ala Leu Ser Asn
            690                 695                 700
Lys Leu Lys Leu Lys Arg Gln Leu Glu Tyr Glu Lys Gln Ala Phe Gln
705                 710                 715                 720
Asp Pro Ser Gly Gly Asp Pro Gly Gly Ser Thr Ser His Leu Met
                    725                 730                 735
Trp Lys Arg Met Lys Asn Leu Arg Gly Gly Ser Cys Pro Leu Met Pro
            740                 745                 750
```

```
Asp Lys Pro Leu Ser Ala Asn Val Pro Asn Asp Lys Leu Thr Gln Asn
            755                 760                 765
Ser Met Arg Gly Leu Gly His Pro Leu Arg His Leu Pro Leu Pro Gln
        770                 775                 780
Pro Pro Ser Ala Ile Ser Pro Gly Glu Asn Ser Lys Ser Arg Phe Pro
785                 790                 795                 800
Pro Gln Cys Tyr Ala Thr Gln Tyr Gln Asp Tyr Ser Leu Ser Ser Ala
            805                 810                 815
His Lys Val Ser Gly Met Ala Ser Arg Leu Leu Gly Pro Ser Phe Glu
            820                 825                 830
Ser Tyr Leu Leu Pro Glu Leu Thr Arg Tyr Asp Arg Glu Val Lys Val
            835                 840                 845
Pro Val Leu Gly Ser Ser Thr Leu Leu Gln Gly Gly Asp Leu Leu Arg
    850                 855                 860
Ala Leu Asp Gln Ala Thr
865                 870

<210> SEQ ID NO 5
<211> LENGTH: 826
<212> TYPE: PRT
<213> ORGANISM: Artificial Sequence
<220> FEATURE:
<223> OTHER INFORMATION: Description of Artificial Sequence: HIF Mutein

<400> SEQUENCE: 5

Met Glu Gly Ala Gly Gly Ala Asn Asp Lys Lys Lys Ile Ser Ser Glu
 1               5                  10                  15
Arg Arg Lys Glu Lys Ser Arg Asp Ala Ala Arg Ser Arg Arg Ser Lys
            20                  25                  30
Glu Ser Glu Val Phe Tyr Glu Leu Ala His Gln Leu Pro Leu Pro His
        35                  40                  45
Asn Val Ser Ser His Leu Asp Lys Ala Ser Val Met Arg Leu Thr Ile
    50                  55                  60
Ser Tyr Leu Arg Val Arg Lys Leu Leu Asp Ala Gly Asp Leu Asp Ile
65                  70                  75                  80
Glu Asp Asp Met Lys Ala Gln Met Asn Cys Phe Tyr Leu Lys Ala Leu
                85                  90                  95
Asp Gly Phe Val Met Val Leu Thr Asp Asp Gly Asp Met Ile Tyr Ile
            100                 105                 110
Ser Asp Asn Val Asn Lys Tyr Met Gly Leu Thr Gln Phe Glu Leu Thr
        115                 120                 125
Gly His Ser Val Phe Asp Phe Thr His Pro Cys Asp His Glu Glu Met
    130                 135                 140
Arg Glu Met Leu Thr His Arg Asn Gly Leu Val Lys Lys Gly Lys Glu
145                 150                 155                 160
Gln Asn Thr Gln Arg Ser Phe Phe Leu Arg Met Lys Cys Thr Leu Thr
                165                 170                 175
Ser Arg Gly Arg Thr Met Asn Ile Lys Ser Ala Thr Trp Lys Val Leu
            180                 185                 190
His Cys Thr Gly His Ile His Val Tyr Asp Thr Asn Ser Asn Gln Pro
        195                 200                 205
Gln Cys Gly Tyr Lys Lys Pro Pro Met Thr Cys Leu Val Leu Ile Cys
    210                 215                 220
Glu Pro Ile Pro His Pro Ser Asn Ile Glu Ile Pro Leu Asp Ser Lys
225                 230                 235                 240
```

-continued

```
Thr Phe Leu Ser Arg His Ser Leu Asp Met Lys Phe Ser Tyr Cys Asp
            245                 250                 255
Glu Arg Ile Thr Glu Leu Met Gly Tyr Glu Pro Glu Leu Leu Gly
        260                 265                 270
Arg Ser Ile Tyr Glu Tyr Tyr His Ala Leu Asp Ser Asp His Leu Thr
            275                 280                 285
Lys Thr His His Asp Met Phe Thr Lys Gly Gln Val Thr Thr Gly Gln
        290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
        355                 360                 365
Met Lys Met Thr Gln Leu Phe Thr Lys Val Glu Ser Glu Asp Thr Ser
    370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
            420                 425                 430
Asp Val Met Leu Pro Ser Pro Asn Glu Lys Leu Gln Asn Ile Asn Leu
        435                 440                 445
Ala Met Ser Pro Leu Pro Thr Ala Glu Thr Pro Lys Pro Leu Arg Ser
    450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
        500                 505                 510
Pro Asn Ser Pro Ser Glu Tyr Cys Phe Tyr Val Asp Ser Asp Met Val
            515                 520                 525
Asn Glu Phe Lys Leu Glu Leu Val Glu Lys Leu Phe Ala Glu Asp Thr
    530                 535                 540
Glu Ala Lys Asn Pro Phe Ser Thr Gln Asp Thr Asp Leu Asp Leu Glu
545                 550                 555                 560
Met Ala Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
            580                 585                 590
Ala Ser Pro Gln Ser Thr Val Thr Val Phe Gln Gln Thr Gln Ile Gln
        595                 600                 605
Glu Pro Thr Ala Asn Ala Thr Thr Thr Thr Ala Thr Thr Asp Glu Leu
    610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                645                 650                 655
```

```
Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
            805                 810                 815

Glu Leu Leu Arg Ala Leu Asp Gln Val Asn
            820                 825

<210> SEQ ID NO 6
<211> LENGTH: 826
<212> TYPE: PRT
<213> ORGANISM: Artificial Sequence
<220> FEATURE:
<223> OTHER INFORMATION: Description of Artificial Sequence: HIF Mutein

<400> SEQUENCE: 6

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190
```

-continued

```
His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser His Leu Thr
    275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
    355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
    435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
    515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Ala Ala Ala Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
    595                 600                 605

Glu Pro Thr Ala Asn Ala Thr Thr Thr Thr Ala Thr Thr Asp Glu Leu
```

-continued

```
                610                 615                 620
Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
                675                 680                 685

Asn Val Leu Ser Val Ala Leu Ser Gln Arg Thr Thr Val Pro Glu Glu
690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
                740                 745                 750

Lys Arg Val Lys Gly Cys Lys Ser Ser Glu Gln Asn Gly Met Glu Gln
                755                 760                 765

Lys Thr Ile Ile Leu Ile Pro Ser Asp Leu Ala Cys Arg Leu Leu Gly
                770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
                820                 825

<210> SEQ ID NO 7
<211> LENGTH: 826
<212> TYPE: PRT
<213> ORGANISM: Artificial Sequence
<220> FEATURE:
<223> OTHER INFORMATION: Description of Artificial Sequence: HIF Mutein

<400> SEQUENCE: 7

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
                35                  40                  45

Asn Val Ser Ser His Leu Asp Lys Ala Ser Val Met Arg Leu Thr Ile
                50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
                115                 120                 125

Gly His Ser Val Phe Asp Phe Thr His Pro Cys Asp His Glu Glu Met
                130                 135                 140

Arg Glu Met Leu Thr His Arg Asn Gly Leu Val Lys Lys Gly Lys Glu
```

```
                145                 150                 155                 160
Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
                180                 185                 190

His Cys Thr Gly His Ile His Val Tyr Asp Thr Asn Ser Asn Gln Pro
                195                 200                 205

Gln Cys Gly Tyr Lys Lys Pro Pro Met Thr Cys Leu Val Leu Ile Cys
                210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
                275                 280                 285

Lys Thr His His Asp Met Phe Thr Lys Gly Gln Val Thr Thr Gly Gln
                290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
                355                 360                 365

Met Lys Met Thr Gln Leu Phe Thr Lys Val Glu Ser Glu Asp Thr Ser
                370                 375                 380

Ser Leu Phe Asp Lys Leu Lys Lys Glu Pro Asp Ala Leu Thr Leu Leu
385                 390                 395                 400

Ala Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
                435                 440                 445

Ala Met Ser Pro Leu Pro Thr Ala Glu Thr Pro Lys Pro Leu Arg Ser
                450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
                515                 520                 525

Asn Glu Phe Lys Leu Glu Leu Val Glu Lys Leu Phe Ala Glu Asp Thr
                530                 535                 540

Glu Ala Lys Asn Pro Phe Ser Thr Gln Asp Thr Asp Leu Asp Leu Glu
545                 550                 555                 560

Met Ala Ala Ala Tyr Ile Pro Met Asp Asp Asp Phe Gln Leu Arg Ser
                565                 570                 575
```

-continued

```
Phe Asp Gln Leu Ser Pro Leu Glu Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
            645                 650                 655

Ser Pro Tyr Arg Asp Thr Gln Ser Arg Thr Ala Ser Pro Asn Arg Ala
        660                 665                 670

Gly Lys Gly Val Ile Glu Gln Thr Glu Lys Ser His Pro Arg Ser Pro
    675                 680                 685

Asn Val Leu Ser Val Ala Leu Ser Gln Arg Thr Thr Val Pro Glu Glu
690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
            725                 730                 735

Leu Leu Gln Gln Pro Asp Asp His Ala Ala Thr Thr Ser Leu Ser Trp
        740                 745                 750

Lys Arg Val Lys Gly Cys Lys Ser Ser Glu Gln Asn Gly Met Glu Gln
    755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
            805                 810                 815

Glu Leu Leu Arg Ala Leu Asp Gln Val Asn
        820                 825

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Conserved
      HIF 8-mer

<400> SEQUENCE: 8

Met Leu Ala Pro Tyr Ile Pro Met
 1               5

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: PCR Primer
      A for Pro564Ala Mutant

<400> SEQUENCE: 9
gcgcggatcc gccaccatgg ag                                              22

<210> SEQ ID NO 10
<211> LENGTH: 27
```

```
<212> TYPE: DNA
<213> ORGANISM: Artificial Sequence
<220> FEATURE:
<223> OTHER INFORMATION: Description of Artificial Sequence: PCR Primer
      B for Pro564Ala Mutant

<400> SEQUENCE: 10
cattgggata taagcagcta acatctc                                          27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: PCR Primer
      C for Pro564Ala Mutant

<400> SEQUENCE: 11
gagatgttag ctgcttatat cccaatg                                          27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: PCR Primer
      D for Pro564Ala Mutant

<400> SEQUENCE: 12
gcgccaattg tcagttaact tg                                               22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: PCR Primer
      A for Pro531Ala mutant

<400> SEQUENCE: 13
gcgcggatcc gccaccatga ca                                               22

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer B
      for Pro531Ala Mutant

<400> SEQUENCE: 14
catggggata taagctgcca gtgtctc                                          27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: PCR Primer
      C for Pro531Ala Mutant

<400> SEQUENCE: 15
gagacactgg cagcttatat ccccatg                                          27

<210> SEQ ID NO 16
<211> LENGTH: 25
<212> TYPE: DNA
```

```
<213> ORGANISM: Artificial Sequence
<220> FEATURE:
<223> OTHER INFORMATION: Description of Artificial Sequence: PCR PrimerD
      for Pro531Ala Mutant

<400> SEQUENCE: 16
gcgccaattg tcaggtggcc tggtc                                          25

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Met Leu Ala Pro Tyr Ile Pro Met
  1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Ala Leu Ala Pro Tyr Ile Pro Met
  1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

Met Ala Ala Pro Tyr Ile Pro Met
  1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 20

Met Leu Ala Ala Tyr Ile Pro Met
  1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 21

Met Leu Ala Pro Ala Ile Pro Met
  1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

Met Leu Ala Pro Tyr Ala Pro Met
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Met Leu Ala Pro Tyr Ile Ala Met
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Met Leu Ala Pro Tyr Ile Pro Ala
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

Ala Ala Ala Ala Ala Ala Ala Ala
 1               5

<210> SEQ ID NO 26
<211> LENGTH: 20
<212> TYPE: PRT
<213> ORGANISM: Homo sapiens

<400> SEQUENCE: 26

Asp Leu Asp Leu Glu Met Leu Ala Pro Tyr Ile Pro Met Asp Asp Asp
 1               5                  10                  15

Phe Gln Leu Arg
            20

<210> SEQ ID NO 27
<211> LENGTH: 21
<212> TYPE: PRT
<213> ORGANISM: Homo sapiens

<400> SEQUENCE: 27

Glu Leu Asp Leu Glu Thr Leu Ala Pro Tyr Ile Pro Met Asp Gly Glu
```

-continued

```
                 1               5                  10                 15

Asp Phe Gln Leu Ser
            20

<210> SEQ ID NO 28
<211> LENGTH: 20
<212> TYPE: PRT
<213> ORGANISM: Mus musculus

<400> SEQUENCE: 28

Asp Leu Asp Leu Glu Met Leu Ala Pro Tyr Ile Pro Met Asp Asp
 1               5                  10                 15

Phe Gln Leu Arg
            20

<210> SEQ ID NO 29
<211> LENGTH: 21
<212> TYPE: PRT
<213> ORGANISM: Mus musculus

<400> SEQUENCE: 29

Glu Leu Asp Leu Glu Thr Leu Ala Pro Tyr Ile Pro Met Asp Gly Glu
 1               5                  10                 15

Asp Phe Gln Leu Ser
            20

<210> SEQ ID NO 30
<211> LENGTH: 20
<212> TYPE: PRT
<213> ORGANISM: Mus musculus

<400> SEQUENCE: 30

Thr Leu Asp Leu Glu Met Leu Ala Pro Tyr Ile Ser Met Asp Asp
 1               5                  10                 15

Phe Gln Leu Asn
            20

<210> SEQ ID NO 31
<211> LENGTH: 20
<212> TYPE: PRT
<213> ORGANISM: Xenopus laevis

<400> SEQUENCE: 31

Asp Leu Asp Leu Glu Met Leu Ala Pro Tyr Ile Pro Met Asp Asp
 1               5                  10                 15

Phe Gln Leu Arg
            20

<210> SEQ ID NO 32
<211> LENGTH: 20
<212> TYPE: PRT
<213> ORGANISM: Drosophila melanogaster

<400> SEQUENCE: 32

Phe Glu Ala Phe Ala Met Arg Ala Pro Tyr Ile Pro Ile Asp Asp
 1               5                  10                 15

Met Pro Leu Leu
            20

<210> SEQ ID NO 33
<211> LENGTH: 19
<212> TYPE: PRT
```

```
<213> ORGANISM: Caenorhabditis elegans

<400> SEQUENCE: 33

Glu Pro Asp Leu Ser Cys Leu Ala Pro Phe Val Asp Thr Tyr Asp Met
  1               5                  10                  15

Met Gln Met

<210> SEQ ID NO 34
<211> LENGTH: 8
<212> TYPE: PRT
<213> ORGANISM: Artificial Sequence
<220> FEATURE:
<221> NAME/KEY: VARIANT
<222> LOCATION: (4)
<223> OTHER INFORMATION: Wherein X is a hydroxylated proline
<220> FEATURE:
<223> OTHER INFORMATION: Description of Artificial Sequence:artificial
      peptide

<400> SEQUENCE: 34

Met Leu Ala Xaa Tyr Ile Pro Met
  1               5

<210> SEQ ID NO 35
<211> LENGTH: 8
<212> TYPE: PRT
<213> ORGANISM: Artificial Sequence
<220> FEATURE:
<221> NAME/KEY: VARIANT
<222> LOCATION: (4)
<223> OTHER INFORMATION: Wherein Xaa is hydroxylated proline
<220> FEATURE:
<223> OTHER INFORMATION: Description of Artificial Sequence:artificial
      peptide

<400> SEQUENCE: 35

Met Ala Ala Xaa Tyr Ile Pro Met
  1               5
```